United States Patent
Zacharchuk

(10) Patent No.: US 9,511,063 B2
(45) Date of Patent: Dec. 6, 2016

(54) ANTINEOPLASTIC COMBINATIONS CONTAINING HKI-272 AND VINORELBINE

(71) Applicant: Wyeth LLC, Madison, NJ (US)

(72) Inventor: Charles Michael Zacharchuk, Westford, MA (US)

(73) Assignee: WYETH LLC, New York, NY (US)

( * ) Notice: Subject to any disclaimer, the term of this patent is extended or adjusted under 35 U.S.C. 154(b) by 128 days.

(21) Appl. No.: 13/875,874

(22) Filed: May 2, 2013

(65) Prior Publication Data

US 2014/0107147 A1   Apr. 17, 2014

Related U.S. Application Data

(63) Continuation of application No. 13/404,390, filed on Feb. 24, 2012, now abandoned, which is a continuation of application No. 12/486,153, filed on Jun. 17, 2009, now abandoned.

(60) Provisional application No. 61/073,330, filed on Jun. 17, 2008.

(51) Int. Cl.
| | |
|---|---|
| A61K 31/437 | (2006.01) |
| A61K 31/4745 | (2006.01) |
| A61K 31/4709 | (2006.01) |
| A61N 5/10 | (2006.01) |
| A61K 31/475 | (2006.01) |
| A61K 31/436 | (2006.01) |

(52) U.S. Cl.
CPC .......... *A61K 31/475* (2013.01); *A61K 31/436* (2013.01); *A61K 31/437* (2013.01); *A61K 31/4709* (2013.01); *A61K 31/4745* (2013.01); *A61N 5/10* (2013.01)

(58) Field of Classification Search
CPC ............ A61K 31/437; A61K 31/4745; A61K 31/4709; A61N 5/10
See application file for complete search history.

(56) References Cited

U.S. PATENT DOCUMENTS

| | | | |
|---|---|---|---|
| 4,966,891 A | 10/1990 | Fujiu et al. | |
| 5,362,718 A | 11/1994 | Skotnicki et al. | |
| 5,453,497 A | 9/1995 | Kamiya et al. | |
| 5,472,949 A | 12/1995 | Arasaki et al. | |
| 5,476,932 A | 12/1995 | Brinkman et al. | |
| 5,705,151 A | 1/1998 | Dow et al. | |
| 5,760,041 A | 6/1998 | Wissner et al. | |
| 6,002,008 A | 12/1999 | Wissner et al. | |
| 6,143,764 A | 11/2000 | Kubo et al. | |
| 6,251,912 B1 | 6/2001 | Wissner et al. | |
| 6,277,983 B1 | 8/2001 | Shaw et al. | |
| 6,288,082 B1 | 9/2001 | Wissner et al. | |
| 6,297,258 B1 | 10/2001 | Wissner et al. | |
| 6,384,051 B1 | 5/2002 | Frost et al. | |
| 6,387,371 B1 | 5/2002 | Hudziak et al. | |
| 6,399,063 B1 | 6/2002 | Hudziak et al. | |
| 6,432,979 B1 | 8/2002 | Frost et al. | |
| 6,511,986 B2 | 1/2003 | Zhang et al. | |
| 6,617,333 B2 | 9/2003 | Rabindran et al. | |
| 6,780,996 B2 | 8/2004 | Boschelli et al. | |
| 6,821,515 B1 | 11/2004 | Cleland et al. | |
| 6,821,988 B2 | 11/2004 | Wissner et al. | |
| 7,026,330 B2 | 4/2006 | Grupp et al. | |
| 7,091,213 B2 | 8/2006 | Metcalf et al. | |
| 7,126,025 B2 | 10/2006 | Considine et al. | |
| 7,189,735 B2 | 3/2007 | Dukart et al. | |
| 7,235,564 B2 | 6/2007 | Scott et al. | |
| 7,294,468 B2 | 11/2007 | Bell et al. | |
| 7,297,795 B2 | 11/2007 | Sutherland et al. | |
| 7,306,801 B2 | 12/2007 | Caligiuri et al. | |
| RE40,418 E | 7/2008 | Rabindran et al. | |
| 7,399,865 B2 | 7/2008 | Wissner et al. | |
| 7,846,936 B2 | 12/2010 | Hilberg et al. | |
| 7,897,159 B2 | 3/2011 | Weber | |
| 7,915,402 B2 | 3/2011 | Anderson et al. | |
| 7,943,778 B2 | 5/2011 | Jiang et al. | |
| 7,964,349 B2 | 6/2011 | Bell et al. | |
| 7,982,043 B2 | 7/2011 | Wissner et al. | |
| 8,022,216 B2 | 9/2011 | Lu et al. | |
| 8,105,769 B2 | 1/2012 | Bell et al. | |
| 8,173,814 B2 | 5/2012 | Lu et al. | |
| 8,338,456 B2 | 12/2012 | Coughlin et al. | |
| 8,394,959 B2 | 3/2013 | Lu et al. | |
| 8,465,916 B2 | 6/2013 | Bell et al. | |
| 8,518,446 B2 | 8/2013 | Ashraf et al. | |

(Continued)

FOREIGN PATENT DOCUMENTS

| | | |
|---|---|---|
| CN | 1437942 A | 8/2003 |
| CN | 101185633 A | 5/2008 |

(Continued)

OTHER PUBLICATIONS

Conte, "Evolving Nonendocrine Therapeutic Options for Metastatic Breast Cancer: How Adjuvant Chemotherapy Influences Treatment", Clinical Breast Cancer, vol. 7, Issue 11, Dec. 2007, pp. 841-849.*

(Continued)

*Primary Examiner* — Sahar Javanmard
(74) *Attorney, Agent, or Firm* — Jones Day

(57) ABSTRACT

A combination of HKI-272 compound and a vinorelbine compound in the treatment of a neoplasm is provided. Regimens, kits, and methods for treatment of neoplasm, including breast cancer including metastatic breast cancer, and lung cancer, using this combination, optionally in combination with other anti-neoplastic agents, or immune modulators are also described.

46 Claims, No Drawings

(56) References Cited

U.S. PATENT DOCUMENTS

| | | |
|---|---|---|
| 8,524,281 B2 | 9/2013 | Venkata Ramana Rao et al. |
| 8,669,273 B2 | 3/2014 | Zacharchuk et al. |
| 8,790,708 B2 | 7/2014 | Ashraf et al. |
| 2002/0002162 A1 | 1/2002 | Lee |
| 2002/0183239 A1 | 12/2002 | Gibbons, Jr. et al. |
| 2002/0183240 A1 | 12/2002 | Gibbons et al. |
| 2002/0198137 A1 | 12/2002 | Dukart et al. |
| 2003/0144252 A1 | 7/2003 | Furr |
| 2003/0149056 A1 | 8/2003 | Wissner et al. |
| 2003/0153593 A1 | 8/2003 | Dukart et al. |
| 2004/0039010 A1 | 2/2004 | Grupp et al. |
| 2004/0162442 A1 | 8/2004 | Considine et al. |
| 2004/0176339 A1 | 9/2004 | Sherman et al. |
| 2004/0209930 A1 | 10/2004 | Carboni et al. |
| 2004/0258662 A1 | 12/2004 | Gibbons et al. |
| 2005/0025825 A1 | 2/2005 | Heasley et al. |
| 2005/0032825 A1 | 2/2005 | Metcalf et al. |
| 2005/0038080 A1 | 2/2005 | Boyer et al. |
| 2005/0043233 A1 | 2/2005 | Stefanic et al. |
| 2005/0059678 A1 | 3/2005 | Wissner et al. |
| 2005/0129761 A1 | 6/2005 | Venkata Ramana Rao et al. |
| 2005/0136063 A1 | 6/2005 | Wang et al. |
| 2005/0187184 A1 | 8/2005 | Gibbons, Jr. et al. |
| 2005/0272083 A1 | 12/2005 | Seshagiri |
| 2005/0272758 A1 | 12/2005 | Bayever et al. |
| 2006/0030547 A1 | 2/2006 | Dukart et al. |
| 2006/0035904 A1 | 2/2006 | Gibbons et al. |
| 2006/0058311 A1 | 3/2006 | Munzert et al. |
| 2006/0079515 A1 | 4/2006 | Frost |
| 2006/0084666 A1 | 4/2006 | Harari et al. |
| 2006/0094674 A1 | 5/2006 | Neel et al. |
| 2006/0128793 A1 | 6/2006 | Zask et al. |
| 2006/0147959 A1 | 7/2006 | Bell et al. |
| 2006/0178387 A1 | 8/2006 | Fujimoto/Ouchi et al. |
| 2006/0235046 A1 | 10/2006 | Zacharchuk et al. |
| 2006/0270668 A1 | 11/2006 | Chew et al. |
| 2006/0270669 A1 | 11/2006 | Chew et al. |
| 2007/0014859 A1 | 1/2007 | Shah et al. |
| 2007/0104721 A1 | 5/2007 | Moore et al. |
| 2007/0105887 A1 | 5/2007 | Moore |
| 2007/0281932 A1 | 12/2007 | Bernier et al. |
| 2008/0096212 A1 | 4/2008 | Bell et al. |
| 2008/0112888 A1 | 5/2008 | Wang |
| 2008/0166359 A1 | 7/2008 | Lamb |
| 2008/0193448 A1 | 8/2008 | Baum |
| 2008/0207615 A1 | 8/2008 | Bell et al. |
| 2008/0234264 A1 | 9/2008 | Bell et al. |
| 2008/0254040 A1 | 10/2008 | Stefanic et al. |
| 2008/0268034 A1 | 10/2008 | Karanth et al. |
| 2008/0286771 A1 | 11/2008 | Hudson et al. |
| 2008/0286785 A1 | 11/2008 | Nishio et al. |
| 2009/0035269 A1 | 2/2009 | Weber |
| 2009/0047278 A1 | 2/2009 | Owa et al. |
| 2009/0060873 A1 | 3/2009 | Sporn et al. |
| 2009/0176827 A1 | 7/2009 | Lu et al. |
| 2009/0203709 A1 | 8/2009 | Steinberg et al. |
| 2009/0246198 A1 | 10/2009 | Dong et al. |
| 2009/0297519 A1 | 12/2009 | Moore et al. |
| 2009/0306101 A1 | 12/2009 | Solca et al. |
| 2009/0312360 A1 | 12/2009 | Zacharchuk |
| 2009/0317456 A1 | 12/2009 | Karrasch et al. |
| 2009/0318480 A1 | 12/2009 | Solca |
| 2009/0325877 A1 | 12/2009 | Grunt et al. |
| 2010/0041904 A1 | 2/2010 | Jiang et al. |
| 2010/0048540 A1 | 2/2010 | Boyle et al. |
| 2010/0048892 A1 | 2/2010 | Anderson et al. |
| 2010/0056777 A1 | 3/2010 | Anderson et al. |
| 2010/0069340 A1 | 3/2010 | Zacharchuk et al. |
| 2010/0081632 A1 | 4/2010 | Oksenberg et al. |
| 2010/0087482 A1 | 4/2010 | Haber et al. |
| 2010/0092490 A1 | 4/2010 | Uenaka et al. |
| 2010/0105031 A1 | 4/2010 | Matsui et al. |
| 2010/0113474 A1 | 5/2010 | Zacharhuk et al. |
| 2010/0120072 A1 | 5/2010 | Lorence et al. |
| 2010/0120768 A1 | 5/2010 | Steinberg et al. |
| 2010/0143340 A1 | 6/2010 | Kolhe et al. |
| 2010/0143350 A1 | 6/2010 | Green et al. |
| 2010/0166744 A1 | 7/2010 | Wong |
| 2010/0189773 A1 | 7/2010 | Mortimore et al. |
| 2010/0226943 A1 | 9/2010 | Brennan et al. |
| 2010/0297118 A1 | 11/2010 | Macdougall et al. |
| 2010/0298760 A1 | 11/2010 | Olle et al. |
| 2010/0310503 A1 | 12/2010 | Li et al. |
| 2011/0014117 A1 | 1/2011 | Wang et al. |
| 2011/0045459 A1 | 2/2011 | Mischel et al. |
| 2011/0052570 A1 | 3/2011 | Klagsbrun et al. |
| 2011/0091421 A1 | 4/2011 | Mann |
| 2011/0091524 A1 | 4/2011 | Wang et al. |
| 2011/0097340 A1 | 4/2011 | Ramachandra et al. |
| 2011/0104256 A1 | 5/2011 | Wang et al. |
| 2011/0111018 A1 | 5/2011 | Ashraf et al. |
| 2011/0112180 A1 | 5/2011 | Jiang et al. |
| 2011/0129456 A1 | 6/2011 | Wang et al. |
| 2011/0165257 A1 | 7/2011 | Rao et al. |
| 2012/0071507 A1 | 3/2012 | Berkenblit et al. |
| 2012/0270896 A1 | 10/2012 | Zacharchuk |
| 2012/0308560 A1 | 12/2012 | Moore et al. |
| 2013/0189274 A1 | 7/2013 | Berkenblit et al. |
| 2013/0281488 A1 | 10/2013 | Lu et al. |
| 2013/0316935 A1 | 11/2013 | Bell et al. |
| 2014/0004203 A1 | 1/2014 | Rao et al. |
| 2014/0050721 A1 | 2/2014 | Moore et al. |
| 2014/0171384 A1 | 6/2014 | Zacharchuk et al. |

FOREIGN PATENT DOCUMENTS

| | | |
|---|---|---|
| EP | 0693285 A2 | 1/1996 |
| EP | 1448531 B1 | 8/2007 |
| EP | 1663978 B1 | 11/2007 |
| EP | 1854463 A1 | 11/2007 |
| EP | 1978106 A1 | 10/2008 |
| EP | 1951274 B1 | 12/2009 |
| EP | 1848414 B1 | 4/2011 |
| EP | 1859793 B1 | 4/2011 |
| JP | 2003-519698 A | 6/2003 |
| JP | 2007-145745 A | 6/2007 |
| WO | WO 92/22653 A1 | 12/1992 |
| WO | WO 95/28406 A1 | 10/1995 |
| WO | WO 96/33978 A1 | 10/1996 |
| WO | WO 96/33980 A1 | 10/1996 |
| WO | WO 98/43960 A1 | 10/1998 |
| WO | WO 00/18761 A1 | 4/2000 |
| WO | WO 01/23395 A2 | 4/2001 |
| WO | WO 01/51919 A2 | 7/2001 |
| WO | WO 02/080975 A1 | 10/2002 |
| WO | WO 02/098416 A2 | 12/2002 |
| WO | WO 02/102976 A2 | 12/2002 |
| WO | WO 03/050090 A1 | 6/2003 |
| WO | WO 03/103676 A2 | 12/2003 |
| WO | WO 2004/004644 A2 | 1/2004 |
| WO | WO 2004/066919 A2 | 8/2004 |
| WO | WO 2004/078133 A2 | 9/2004 |
| WO | WO 2004/093854 A2 | 11/2004 |
| WO | WO 2004/096224 A2 | 11/2004 |
| WO | WO 2005/018677 A2 | 3/2005 |
| WO | WO 2005/032513 A2 | 4/2005 |
| WO | WO 2005/034955 A1 | 4/2005 |
| WO | WO 2005/037287 A1 | 4/2005 |
| WO | WO 2005/044091 A2 | 5/2005 |
| WO | WO 2005/049021 A1 | 6/2005 |
| WO | WO 2005/087265 A1 | 9/2005 |
| WO | WO 2005/094357 A2 | 10/2005 |
| WO | WO 2006/044453 A1 | 4/2006 |
| WO | WO 2006/044748 A2 | 4/2006 |
| WO | WO 2006/081985 A1 | 8/2006 |
| WO | WO 2006/084058 A2 | 8/2006 |
| WO | WO 2006/095185 A1 | 9/2006 |
| WO | WO 2006/098978 A1 | 9/2006 |
| WO | WO 2006/113151 A2 | 10/2006 |
| WO | WO 2006/113304 A2 | 10/2006 |
| WO | WO 2006/116514 A2 | 11/2006 |
| WO | WO 2006/120557 A1 | 11/2006 |
| WO | WO 2006/120573 A2 | 11/2006 |
| WO | WO 2006/127205 A2 | 11/2006 |

(56) References Cited

FOREIGN PATENT DOCUMENTS

| | | |
|---|---|---|
| WO | WO 2006/127207 A1 | 11/2006 |
| WO | WO 2007/000234 A1 | 1/2007 |
| WO | WO 2007/011619 A2 | 1/2007 |
| WO | WO 2007/056118 A1 | 5/2007 |
| WO | WO 2007/075794 A2 | 7/2007 |
| WO | WO 2007/095038 A2 | 8/2007 |
| WO | WO 2007/116025 A2 | 10/2007 |
| WO | WO 2007/130438 A2 | 11/2007 |
| WO | WO 2007/137187 A2 | 11/2007 |
| WO | WO 2007/139797 A2 | 12/2007 |
| WO | WO 2008/076143 A1 | 6/2008 |
| WO | WO 2008/076278 A2 | 6/2008 |
| WO | WO 2008/089087 A2 | 7/2008 |
| WO | WO 2008/093878 A1 | 8/2008 |
| WO | WO 2008/121467 A2 | 10/2008 |
| WO | WO 2008/127710 A2 | 10/2008 |
| WO | WO 2008/130910 A1 | 10/2008 |
| WO | WO 2009/036099 A1 | 3/2009 |
| WO | WO 2009/042613 A1 | 4/2009 |
| WO | WO 2009/052264 A2 | 4/2009 |
| WO | WO 2009/061349 A1 | 5/2009 |
| WO | WO 2009/105234 A2 | 8/2009 |
| WO | WO 2009/108637 A1 | 9/2009 |
| WO | WO 2009/111073 A2 | 9/2009 |
| WO | WO 2009/121031 A1 | 10/2009 |
| WO | WO 2009/126662 A1 | 10/2009 |
| WO | WO 2009/129545 A1 | 10/2009 |
| WO | WO 2009/129546 A1 | 10/2009 |
| WO | WO 2009/129548 A1 | 10/2009 |
| WO | WO 2009/146216 A2 | 12/2009 |
| WO | WO 2009/146218 A2 | 12/2009 |
| WO | WO 2009/151910 A2 | 12/2009 |
| WO | WO 2010/008744 A2 | 1/2010 |
| WO | WO 2010/011782 A1 | 1/2010 |
| WO | WO 2010/045318 A2 | 4/2010 |
| WO | WO 2010/048477 A2 | 4/2010 |
| WO | WO 2010/054051 A1 | 5/2010 |
| WO | WO 2010/085845 A1 | 8/2010 |
| WO | WO 2010/091140 A1 | 8/2010 |
| WO | WO 2010/098627 A2 | 9/2010 |
| WO | WO 2010/104406 A1 | 9/2010 |
| WO | WO 2010/117633 A1 | 10/2010 |
| WO | WO 2010/120861 A1 | 10/2010 |
| WO | WO 2010/124009 A2 | 10/2010 |
| WO | WO 2010/129053 A2 | 11/2010 |
| WO | WO 2011/002857 A2 | 1/2011 |
| WO | WO 2011/008053 A2 | 1/2011 |
| WO | WO 2011/008054 A2 | 1/2011 |
| WO | WO 2011/025267 A2 | 3/2011 |
| WO | WO 2011/025269 A2 | 3/2011 |
| WO | WO 2011/025271 A2 | 3/2011 |
| WO | WO 2011/025720 A1 | 3/2011 |
| WO | WO 2011/038467 A1 | 4/2011 |
| WO | WO 2011/056741 A2 | 5/2011 |
| WO | WO 2011/060206 A2 | 5/2011 |
| WO | WO 2011/069962 A1 | 6/2011 |
| WO | WO 2011/070499 A1 | 6/2011 |

OTHER PUBLICATIONS

Al-Muhammed, J. Microencapsul. 13:293-306, (1996).
Azrla et al. Bull. Cancer, 2003, vol. 90, pp. S202-S212 (Abstract).
Berstein et al. Breast Cancer Research and Treatment, vol. 106, suppl. 1, Dec. 2007, Abstract #6061, p. S268.
Chonn, Curr. Opin. Biotechnol., 6:698-708 (1995).
Eyles, J. Pharm. Pharmacol., 49:669-674 (1997).
Gao, Pharm. Res., 12:857-863 (1995).
Jahanzeb et al. The Oncologist, 2002, vol. 7, pp. 410-417.
Johnson, S.W., Stevenson, J.P., O'Dwyer, P.J., "Cisplatin and its Analogues," Cancer Principles & Practice of Oncology, 6th edition, ed. Devita, V.T., Hellman, S., Rosenberg, S.A, Lippincott Williams & Wilkins. Philadelphia, 2001, p. 378.
Langlois et al., J. Am. Chem. Soc., 98:7017-7024 (1976).
Mangeney et al., Tetrahedron, 35:2175-2179 (1979).
Ostro, Am. J. Hosp. Pharm., 46:1576-1587 (1989).
Practice Guidelines from the American Society of Clinical Oncology (ASCO; 2006).
Rabindran et al. Cancer Res., 2004, vol. 64, pp. 3958-3965.
Rao, J. Biomater Sci. Polym. Ed., 7:623-645 (1995).
Remington's Pharmaceutical Sciences, 17th edition, Alfonso R. Gennaro, Mack Publishing Company, Easton, PA (1985).
Widakowich et al., Anticancer Agents Med. Chem., 8(5):488-496 (Jun. 2008).
Wissner et al., Arch. Pharm. (Weinheim), May 20, 2008, e-publication.
Wong, K. Clin. Cancer Res., 2007, vol. 13, pp. 4593s-4596s.
"Trastuzumab." Wikipedia: Wikipedia: The Free Encyclopedia. Wikimedia Foundation, Inc. Retrieved from the Internet Aug. 14, 2009. URL:http://en.wikipedia.org/wiki/Herceptin.
"Vinorelbin." *Wikipedia: The Free Encyclopedia*. Wikimedia Foundation, Inc. Retrieved from the Internet on Jan. 28, 2013. URL:http://en.wikipedia.org/wiki/Vinorelbine.
Abbas et al., "A Drug Interaction Study to Evaluate the Effect of Ketoconazole on the Pharmacokinetics (PK) of Neratinib in Healthy Subjects," Clin. Pharmacol. Therapeutics 85:s44 (2009).
Abbas et al., "Evaluation of Neratinib (HKI-272) and Paclitaxel Pharmacokinetics (PK) in Asian and Caucasian Patients with Erbb2+ Breast Cancer: a Phase 1/2 Study of Neratinib in Combination with Paclitaxel," Ann. Oncol. 21:101 (2010).
Abbas et al., "Pharmacokinetics of Oral Neratinib During Co-Administration of Ketoconazole in Healthy Subjects," Br. J. Clin. Pharmacol. 71(4):522-527 (2011).
Abbas-Borhan et al., "A Clinical Study to Characterize the Occurrence of Mild-to-Moderate Diarrhea After Administration of Neratinib Either Once Daily or Twice Daily for 14 Days," EJC Suppl. 8:143 (2010).
Abbas-Borhan et al., "An Open-Label Study to Assess the Mass Balance and Metabolic Disposition of an Orally Administered Single Dose of 14C-Labeled Neratinib, an Irreversible pan-ErbB inhibitor, in Healthy Subjects," Drug Metab. Rev. 42:S1, 216 Abstr. P330 (2010).
Abrams et al., "Preclinical evaluation of the tyrosine kinase inhibitor SU11248 as a single agent and in combination with "standard of care" therapeutic agents for the treatment of breast cancer," Mol. Cancer Ther. 2(10):1011-1021 (2003).
Abramson and Arteaga, "New Strategies in HER2-Overexpressing Breast Cancer: Many Combinations of Targeted Drugs Available," Clin. Cancer Res. 17:952-958 (2011).
Adelaide et al., "Integrated Profiling of Basal and Luminal Breast Cancers," Cancer Res. 67(24):11565-11575 (2007).
Al-Dasooqi et al., "HER2 Targeted Therapies for Cancer and the Gastrointestinal Tract," Curr. Drug Targets 10(6):537-542 (2009).
Ali et al., "Mutational Spectra of PTEN/MMAC1 Gene: a Tumor Suppressor with Lipid Phosphatase Activity," J. Natl. Cancer Inst. 91(22):1922-1932 (1999).
Allegra et al., "American Society of Clinical Oncology Provisional Clinical Opinion: Testing for KRAS Gene Mutations in Patients With Metastatic Colorectal Carcinoma to Predict Response to Anti—Epidermal Growth Factor Receptor Monoclonal Antibody Therapy," J. Clin. Oncol. 27(12):2091-2096 (2009).
Alvarez et al., "Emerging Targeted Therapies for Breast Cancer," J. Clin. Oncol. 28(20):3366-3379 (2010).
Álvarez, "Present and Future Evolution of Advanced Breast Cancer Therapy," Breast Cancer Res. 12(Suppl 2):S1 (2010).
Amslinger, "The tunable functionality of alpha,beta-unsaturated carbonyl compounds enables their differential application in biological systems," ChemMedChem. 5(3):351-356 (2010).
Andre and Diniz, "Targeted regimes without cytotoxics—are they ready for prime time?" EJC Suppl. 7:49 Abst. 191 (2009).
Andre et al., "Everolimus for women with trastuzumab-resistant, HER2-positive, advanced breast cancer (BOLERO-3): a randomised, double-blind, placebo-controlled phase 3 trial," Lancet Oncol. 15(6):580-591 (2014) (Epub Apr. 14, 2014).
Anonymous, "Trastuzumab", Wikipedia, Retrieved from the Internet on Nov. 21, 2014. URL:http://en.wikipedia.org/wiki/Trastuzumab?oldid=634842165.

(56) References Cited

OTHER PUBLICATIONS

Anonymous: "Meeting Archives of Chemotherapy Foundation Symposium XXIV, Nov. 7-10, 2007", The Chemotherapy Foundation, Nov. 8, 2007, Retrieved from the Internet on Jan. 13, 2010: URL:http://www.chemotherapyfoundationsymposium.org/meeting_archives/meetingarchives_tcf2007_main.html.
Anonymous: "Anticancer Agent—neratinib", Manufacturing Chemist, Dec. 2010/Jan. 2011, p. 27.
Arteaga, "ErbB-targeted therapeutic approaches in human cancer," Exp. Cell. Res. 284(1):122-130 (2003).
Awada and Piccart-Gebhart, "Management of HER-2/Neu-Positive Metastatic Breast Cancer," Eur. J. Cancer (Suppl. 6):2-9 (2008).
Awada et al., "Safety and Efficacy of Neratinib (HKI-272) in Combination with Vinorelbine in ErbB2+ Metastatic Breast Cancer," Cancer Res. 69:24(Suppl 3) Abstr. 5095 (2009).
Awada et al., "Safety and Efficacy of Neratinib (HKI-272) in Combination with Vinorelbine in ErbB2+ Metastatic Breast Cancer (MBC)," Ann. Oncol. 21(Suppl. 4):iv62-iv63 Abstr. 145P (2010).
Awada et al., "Safety and efficacy of neratinib (HKI-272) plus vinorelbine in the treatment of patients with ErbB2-positive metastatic breast cancer pretreated with anti-HER2 therapy," Ann. Oncol. 24(1):109-116 (2013) (Epub Sep. 11, 2012).
Azria et al., "[Radiotherapy and inhibitors of epidermal growth factor receptor: preclinical findings and preliminary clinical trials]," Bull Cancer 90 Spec No:S202-S212 (2003). (Abstract only).
Badache and Goncalves, "The ErbB2 signaling network as a target for breast cancer therapy," J. Mammary Gland Biol. Neoplasia 11(1):13-25 (2006).
Barton et al., "Predictive molecular markers of response to epidermal growth factor receptor(EGFR) family-targeted therapies," Curr. Cancer Drug Targets 10(8):799-812 (2010).
Baselga and Swain, "Novel anticancer targets: revisiting ERBB2 and discovering ERBB3," Nat. Rev. Cancer 9(7):463-475 (2009) (Epub Jun. 18, 2009).
Baselga et al., "Phase I safety, pharmacokinetic, and pharmacodynamic trial of ZD1839, a selective oral epidermal growth factor receptor tyrosine kinase inhibitor, in patients with five selected solid tumor types," J. Clin. Onc. 20(21):4292-4302 (2002).
Baselga, "Is there a role for the irreversible epidermal growth factor receptor inhibitor EKB-569 in the treatment of cancer? A mutation-driven question," J. Clin. Oncol. 24(15):2225-2226 (2006).
Baselga, "Novel agents in the era of targeted therapy: what have we learned and how has our practice changed?" Ann. Oncol. 19(Suppl 7):vii281-vii288 (2008).
Baselga, "Treatment of HER2-Overexpressing Breast Cancer," Ann. Oncol. (Suppl 7):vii36-vii40 (2010).
Bayes et al., "Gateways to clinical trials," Methods Find. Exp. Clin. Pharmacol. 28(9):657-678 (2006).
Bedard et al., "Beyond trastuzumab: overcoming resistance to targeted HER-2 therapy in breast cancer," Curr. Cancer Drug Targets 9(2):148-162 (2009).
Bedard et al., "Stemming resistance to HER-2 targeted therapy," J. Mammary Gland Biol. Neoplasia 14(1):55-66 (2009) (Epub Mar. 4, 2009).
Belani, "The role of irreversible EGFR inhibitors in the treatment of non-small cell lung cancer: overcoming resistance to reversible EGFR inhibitors," Cancer Invest. 28(4):413-423 (2010).
Bell and Haber, "A blood-based test for epidermal growth factor receptor mutations in lung cancer," Clin. Cancer Res. 12(13):3875-3877 (2006).
Berns et al., "A functional genetic approach identifies the PI3K pathway as a major determinant of trastuzumab resistance in breast cancer," Cancer Cell 12(4):395-402 (2007).
Berz and Wanebo, "Targeting the growth factors and angiogenesis pathways: small molecules in solid tumors," J. Surg. Oncol. 103(6):574-586 (2011).
Besse et al., "Neratinib (HKI-272), an irreversible pan-ErbB receptor tyrosine kinase inhibitor: preliminary results of a phase 2 trial in patients with advanced non-small cell lung cancer," Eur. J. Cancer (Suppl.):23 Abstr. 203 (2008).
Besse et al., "Targeted therapies in lung cancer," Ann. Oncol. 18(Suppl. 9):ix135-ix142 (2007).
Bettendorf et al., "Chromosomal imbalances, loss of heterozygosity, and immunohistochemical expression of TP53, RB1, and PTEN in intraductal cancer, intraepithelial neoplasia, and invasive adenocarcinoma of the prostate," Genes Chromosomes Cancer 47(7):565-572 (2008).
Bischoff and Ignatov, "The Role of Targeted Agents in the Treatment of Metastatic Breast Cancer," Breast Care (Basel) 5(3):134-141 (2010) (Epub Jun. 16, 2010).
Blanco-Aparicio et al., "PTEN, More Than the AKT Pathway," Carcinogenesis 28(7):1379-1386 (2007) (Epub Mar. 6, 2007).
Blanke, "Gefitinib in colorectal cancer: if wishes were horses," J. Clin. Oncol. 23(24):5446-5449 (2005).
Blencke et al., "Mutation of threonine 766 in the epidermal growth factor receptor reveals a hotspot for resistance formation against selective tyrosine kinase inhibitors," J. Biol. Chem. 278(17):15435-15440 (2003) (Epub Feb. 19, 2003).
Board et al., "Multiplexed assays for detection of mutations in PIK3CA," Clin. Chem 54(4):757-760 (2008).
Bonanno et al., "Mechanisms of acquired resistance to epidermal growth factor receptor tyrosine kinase inhibitors and new therapeutic perspectives in non small cell lung cancer," Curr. Drug Targets 12(6):922-933 (2011).
Boschelli et al., "Bosutinib: a review of preclinical studies in chronic myelogenous leukaemia," Eur. J. Cancer. 46(10):1781-1789 (2010).
Boschelli, "4-Anilino-3-quinolinecarbonitriles: An Emerging Class of Kinase Inhibitors—An Update," Med. Chem Rev. Online 1:457-463 (2004).
Bose and Ozer, "Neratinib: an oral, irreversible dual EGFR/HER2 inhibitor for breast and non-small cell lung cancer," Expert Opin. Investig. Drugs 18(11):1735-1751 (2009).
Bose et al., "Allelic loss of chromosome 10q23 is associated with tumor progression in breast carcinomas," Oncogene 17(1):123-127 (1998).
Bose et al., "Reduced expression of PTEN correlates with breast cancer progression," Hum. Pathol. 33(4):405-409 (2002).
Boyce et al., "Requirement of pp60c-src expression for osteoclasts to form ruffled borders and resorb bone in mice," J. Clin. Invest. 90(4):1622-1627 (1992).
Boyd et al., "Lapatanib: Oncolytic Dual EFGR and erbB-2 Inhibitor," Drugs Future 30(12):1225-1239 (2005).
Brackstone et al., "Canadian initiatives for locally advanced breast cancer research and treatment: inaugural meeting of the Canadian Consortium for LABC," Curr. Oncol. 18(3):139-144 (2011).
Bridges, "Current Progress Towards the Development of Tyrosine Kinase Inhibitors as Anticancer Agents," Expert Opin. Emerg. Drugs. 3:279-292 (1998).
Brittain, Harry G. (Eds), "Polymorphism in Pharmaceutical Solids", Chapters 1 and 5, Marcel Dekker, Inc., New York (1999).
Brook et al., "Management of transitional cell carcinoma by targeting the epidermal growth factor receptor," Therapy 3(3):407-416 (2006).
Browne et al., "HER-2 Signaling and Inhibition in Breast Cancer," Curr. Cancer Drug Targets 9(3):419-438 (2009).
Broxterman and Georgopapadakou, "Anticancer therapeutics: a surge of new developments increasingly target tumor and stroma," Drug Resist. Updat. 10(4-5):182-193 (2007) (Epub Sep. 12, 2007).
Buerger et al., "Allelic length of a CA dinucleotide repeat in the egfr gene correlates with the frequency of amplifications of this sequence—first results of an inter-ethnic breast cancer study," J. Pathol. 203(1):545-550 (2004).
Bullard Dunn et al., "Evolving Therapies and FAK Inhibitors for the Treatment of Cancer," Anticancer Agents Med. Chem. 10(10):722-734 (2010).
Burstein et al., "Gastrointestinal and Cardiovascular Safety Profiles of Neratinib Monotherapy in Patients with Advanced Erbb2-Positive Breast Cancer," Cancer Res. 69:Abst 5096 (2009).
Burs'Iein et al., "Neratinib (HKI-272), an irreversible pan ErbB receptor tyrosine kinase inhibitor: phase 2 results in patients with advanced HER2+ breast cancer," Cancer Res. 69(2 Suppl.) Abstr. 37 (2009).

(56) References Cited

OTHER PUBLICATIONS

Burstein et al., "Neratinib, an irreversible ErbB receptor tyrosine kinase inhibitor, in patients with advanced ErbB2-positive breast cancer," J. Clin. Oncol. 28(8):1301-1307 (2010).
Burstein, "The Distinctive Nature of HER2-Positive Breast Cancers," N. Engl. J. Med. 353(16):1652-1654 (2005).
Byrn et al., "Pharmaceutical solids: a strategic approach to regulatory considerations," Pharm. Res. 12(7):945-954 (1995).
Callahan and Hurwitz, "Human epidermal growth factor receptor-2-positive breast cancer: Current management of early, advanced, and recurrent disease," Curr. Opin. Obstet. Gynecol. 23(1):37-43 (2011).
Camp et al., "Molecular mechanisms of resistance to therapies targeting the epidermal growth factor receptor," Clin. Cancer Res. 11(1):397-405 (2005).
Campas et al., "BIBW-2992. Dual EGFR/HER2 Inhibitor Oncolytic;Tovok™," Drugs Future 33(8):649-654 (2008).
Campbel et al., "Gefitinib for the Treatment of Non-Small-Cell Lung Cancer," Expert Opin. Pharmacother. 11(8):1343-1357 (2010).
Cao et al., "Epidermal Growth Factor Receptor as a Target for Anti-Cancer Agent Design," Anticancer Agents Med. Chem. 10(6):491-503 (2010).
Cappuzzo et al., "Gefitinib in pretreated non-small-cell lung cancer (NSCLC) analysis of efficacy and correlation with HER2 and epidermal growth factor receptor expression in locally advanced or metastatic NSCLC," J. Clin. Oncol. 21(14):2658-2663 (2003).
Cappuzzo et al., "Surrogate predictive biomarkers for response to anti-EGFR agents: state of the art and challenges," Int. J. Biol. Markers 22(1 Suppl 4):S10-S23 (2007).
Cardoso et al., "Locally Recurrent or Metastatic Breast Cancer: ESMO Clinical Practice Guidelines for Diagnosis, Treatment and Follow-Up," Ann. Oncol. 21(5):v15-v19 (2010).
Carney et al., "HER-2/neu diagnostics in breast cancer," Breast Cancer Res. 9(3):207 (2007).
Carter et al., "Small-Molecule Inhibitors of the Human Epidermal Receptor Family," Expert Opin. Investig. Drugs 18(12):1829-1842 (2009).
Cascone et al., "Epidermal Growth Factor Receptor Inhibitors in Non-Small-Cell Lung Cancer," Expert Opin. Drug Discov. 2(3):335-348 (2007).
Centre de Lutte Conti le Cancer Georges-Francois Leclerc (Fumoleau P. Study chair): "Lapatinib and Vinorelbine in Treating Women With HER2-Overexpressing Locally Advanced or Metastatic Breast Cancel" Clinical Trials Aug. 6, 2007 Retrieved from the Internet: URL:http://clinicaltrials.gov/ct2/show/NCT00513058?term=lapatinib+and+vinorelbine&rank=1 [retrieved on Jan. 13, 2010].
Chan and Giaccia, "Harnessing Synthetic Lethal Interactions in Anticancer Drug Discovery," Nat. Rev. Drug Discov. 10(5):351-364 (2011).
Chan, "A review of the use of trastuzumab (Herceptin®) plus vinorelbine in metastatic breast cancer," Ann. Oncol.18(7):1152-1158 (2007) (Epub Jan. 29, 2007) Review.
Chandrasekaran et al., "Reversible Covalent Binding of Neratinib to Human Serum Albumin in Vitro," Drug Metab. Lett. 4(4):220-227 (2010).
Chen et al., "Epidermal growth factor receptor inhibitors: current status and future directions," Curr. Probl. Cancer 33(4):245-294 (2009).
Chenoweth, "Can single-patient investigational new drug studies hurry slow trains to the fast track?" Drug Discov. Today 11(5-6):185-186 (2006).
Cheung and Paterson, "American Chemical Society—226th National Meeting. Pain and Oncology," Idrugs 6(10):935-936 (2003).
Chew, H. K. et al., EGFR Inhibition with Lapatinib in Combination with Vinorelbine: A Phase I Study, Chemotherapy Foundation Symposium XXV, Chemotherapy Foundation, 2007, [Retrieved on Aug. 30, H-25 (2013)], obtained from the Internet, URL: http://chemotherapyfoundationsymposium.org/CMS/2007-archives-main.
Chew, Helen K., MD (University of California, Davis): "Lapatinib and Vinorelbine in Treating Patients With Advanced Solid Tumors" ClinicalTrials, Oct. 18, 2006, Retrieved from the Internet: URL:http//clinicaltrials.gov/ct2/show/NCT00389922?term=lapatinib+and+vinorelnine&rank=2 [retrieved on Jan. 13, 2010].
Chien and Rugo, "The Cardiac Safety of Tmstuzumab in the Treatment of Breast Cancer," Expert Opin. Drug Saf. 9(2):335-346 (2010).
Chirieac and Dacic, "Targeted Therapies in Lung Cancer," Surg. Pathol. Clin. 3(1):71-82 (2010).
Chmielecki et al. Selection for the EGFR T790M gatekeeper resistance mutation may vary among different small molecule EGFR TKIs [abstract]. In: Proceedings of the 101st Annual Meeting of the American Association for Cancer Research; Apr. 17-21, 2010; Washington, DC. Philadelphia (PA): AACR; Cancer Res 2010;70(8 Suppl):Abstract nr 1774.
Cho et al., "Structure of the extracellular region of HER2 alone and in complex with the Herceptin Fab," Nature 421(6924):756-760 (2003).
Choong et al., "Gefitinib response of erlotinib-refractory lung cancer involving meninges—role of EGFR mutation," Nat. Clin. Pract. Oncol. 3(1):50-57 (2006).
Chow et al., "Safety and efficacy of nemtinib (HKI-272) in combination with paclitaxel in EibB2+ metastatic breast cancer," Cancer Res. (Meeting Abstracts) 69:S5081 (2009).
Chow et al., "Safety and efficacy of nemtinib (HKI-272) in combination with paclitaxel in patients with solid tumors," J. Clin. Oncol. (Meeting Abstracts) 27(15S):3557 (2009).
Chow et al., "Safety and efficacy of neratinib (HKI-272) in combination with paclitaxel in ERBB2+ metastatic breast cancer (MBC)," Ann. Oncol. 21(Suppl 4):iv62 Abstr. 144P (2010).
Cicenas, "The Potential Role of the EGFR/ERBB2 Heterodimer in Breast Cancer," Expert Opin. Ther. Patents 17(6):607-616 (2007).
Clouser et al., "Biomarker Targets and Novel Therapeutics," Cancer Treat. Res. 149:85-105 (2009).
Cobleigh et al., "Multinational study of the efficacy and safety of humanized anti-HER2 monoclonal antibody in women who have HER2-overexpressing metastatic breast cancer that has progressed after chemotherapy for metastatic disease," J. Clin. Oncol. 17(9):2639-2648 (1999).
Cohen et al., "United States Food and Drug Administration Drug Approval summary: Gefitinib (ZD1839; Iressa) tablets," Clin. Cancer Res. 10(4):1212-1218 (2004).
Coldren et al., "Baseline gene expression predicts sensitivity to gefitinib in non-small cell lung cancer cell lines," Mol. Cancer Res. 4(8):521-528 (2006).
Collins et al., "Lapatinib: a competitor or companion to trastuzumab?" Cancer Treat. Rev. 35(7):574-581 (2009).
Colombo et al., "HER2 targeting as a two-sided strategy for breast cancer diagnosis and treatment: Outlook and recent implications in nanomedical approaches," Pharmacol. Res. 62(2):150-165 (2010) (Epub Feb. 1, 2010).
Cooper and Cohen, "Mechanisms of resistance to EGFR inhibitors in head and neck cancer," Head Neck 31(8):1086-1094 (2009).
Correspondence from Chilean associate regarding a First Office Action issued in corresponding Chilean Patent Application No. 2961-2006 in 2009-2010.
Correspondence from Israeli associate regarding a First Office Action issued in corresponding Israeli Patent Application No. 190805 in 2010.
Correspondence from Peruvian associate regarding an Opposition filed against corresponding Peruvian Patent Application No. 001 342-2006/QIN in 2007.
Cortes-Funes et al., "Neratinib, An Irreversible Pan Erb Receptor Tyrosine Kinase Inhibitor Active for Advanced HER2+ Breast Cancer," Breast Cancer Res. 11 Suppl 1:S19 (2009).
Coughlin et al., "Approaches and limitations of phosphatidylinositol-3-kinase pathway activation status as a pre-

(56) References Cited

OTHER PUBLICATIONS dictive biomarker in the clinical development of targeted therapy," Breast Cancer Res. Treat. 124(1):1-11 (2010) (Epub Aug. 28, 2010).
Cox, "Regression Models and Life Tables (With Discussion)," Journal of the Royal Statistical Society. Series B (Methodological), vol. 34, No. 2. (1972), pp. 187-220.
Da Cunha Santos et al., "EGFR Mutations and Lung Cancer," Ann. Rev. Pathol. 6:49-69 (2011).
Damia and D'Incalci, "Contemporary pre-clinical development of anticancer agents—what are the optimal preclinical models?" Eur. J. Cancer 45(16):2768-2781 (2009) (Epub Sep. 15, 2009).
Dancey, "Epidermal growth factor receptor inhibitors in non-small cell lung cancer," Drugs 67(8):1125-1138 (2007).
Dang et al.,"The safety of dose-dense doxorubicin and cyclophosphamide followed by paclitaxel with trastuzumab in HER-2/neu overexpressed/amplified breast cancer," J. Clin. Oncol. 26(8):1216-1222 (2008).
Daniele and Sapino, "Anti-HER2 treatment and breast cancer: state of the art, recent patents, and new strategies," Recent Pat. Anticancer Drug Discov. 4(1):9-18 (2009).
Davidian, M. (2006) Introduction to statistical population modeling and analysis for pharmacokinetic data. Invited white paper for the International Workshop on Uncertainty and Variability in Physiologically Based Pharmacokinetic (PBPK) Models. Retrieved from the Internet: URL:http://www.epa.gov/ncct/uvpkm/files/Calibration_PreMeeting_Draft.pdf (89 pages) [Retrieved on Jan. 29, 2014].
Davidson, "HER2-Targeted Therapies: How Far We've Come-And Where We're Headed," Oncology (Williston Park) 25(5):425-426 (2011).
Davoli et al., "Progression and Treatment of HER2-Positive Breast Cancer," Cancer Chemother. Pharmacol. 65(4):611-623 (2010) (Epub Dec. 20, 2009).
De Bono and Rowinsky, "The ErbB receptor family: a therapeutic target for cancer," Trends Mol. Med. 8(4 Suppl):S19-S26 (2002).
De Luca and Normanno, "Predictive biomarkers to tyrosine kinase inhibitors for the epidermal growth factor receptor in non-small-cell lung cancer," Curr. Drug Targets 11(7):851-864 (2010).
De Maio et al., "Vinorelbine plus 3-weekly trastuzumab in metastatic breast cancer: a single-centre phase 2 trial," BMC Cancer. 7:50 (2007).
De Seranno and Meuwissen, "Progress and Applications of Mouse Models for Human Lung Cancer," Eur. Respir. J. 5(2):426-443 (2010).
Dempke and Heinemann, "Resistance to EGF-R (erbB-1) and VEGF-R modulating agents," Eur. J. Cancer 45(7):1117-1128 (2009) (Epub Jan. 3, 2009).
Depowski et al., "Loss of expression of the PTEN gene protein product is associated with poor outcome in breast cancer," Mod. Pathol. 14(7):672-676 (2001).
Di Cosimo and Baselga, "Management of breast cancer with targeted agents: importance of heterogeneity. [corrected]." Nat. Rev. Clin. Oncol. 7(3):139-147 (2010) (Epub Feb. 2, 2010).
Di Cosimo and Baselga, "Targeted Therapies in Breast Cancer: Where Are We Now?" Eur. J. Cancer 44(18):2781-2790 (2008) (Epub Nov. 14, 2008).
Di Maio et al., "New drugs in advanced non-small-cell lung cancer: searching for the correct clinical development," Expert Opin. Investig. Drugs 19(12):1503-1514 (2010) (Epub Nov. 4, 2010).
Dickler, "Updates on Therapeutic Approaches in HER2-Positive Disease," Clin. Adv. Hematol. Oncol. 8(2):105-107 (2010).
Dinh et al., "Trastuzumab for early breast cancer: current status and future directions," Clin. Adv. Hematol. Oncol. 5(9):707-717 (2007).
Dirix et al., "Neratinib Monotherapy in Patients with Advanced ERBB2-Positive Breast Cancer: Gastrointestinal and Cardiovascular Safety Profiles," Ann. Oncol. 21(Suppl 4):iv61-iv62 Abstr. 141P (2010).
Discafani et al., "Irreversible inhibition of epidermal growth factor receptor tyrosine kinase with in vivo activity by N-[4-[(3-bromophenyl)amino]-6-quinazolinyl]-2-butynamide (CL-387,785)," Biochem. Pharmacol. 57(8):917-925 (1999).
Doebele et al., "New strategies to overcome limitations of reversible EGFR tyrosine kinase inhibitor therapy in non-small cell lung cancer," Lung Cancer 69(1):1-12 (2010) (Epub Jan. 25, 2010).
Dorland's Illustrated Medical Dictionary. 31st ed. Philadelphia: Saunders Elsevier; c2007. Carcinoma; pp. 295-297.
Dowsett and Dunbier, "Emerging Biomarkers and New Understanding of Traditional Markers in Personalized Therapy for Breast Cancer," Clin. Cancer Res. 14(24):8019-8026 (2008).
Druker et al., "Efficacy and Safety of a Specific Inhibitor of the BCR-ABL Tyrosine Kinase in Chronic Myeloid Leukemia," N. Engl. J. Med. 344(14):1031-1037 (2001).
Eck and Yun, "Structural and Mechanistic Underpinnings of the Differential Drug Sensitivity of EGFR Mutations in Non-Small Cell Lung Cancer," Biochim Biophys. Acta 1804(3):559-566 (2010).
Egloff and Grandis, "Targeting epidermal growth factor receptor and SRC pathways in head and neck cancer," Semin Oncol. 35(3):286-297 (2008).
Eichhorn et al., "Phosphatidylinositol 3-kinase hyperactivation results in lapatinib resistance that is reversed by the mTOR/phosphatidylinositol 3-kinase inhibitor NVP-BEZ235," Cancer Res. 68(22):9221-9230 (2008).
Einhorn et al., "Summary Report 7th Annual Targeted Therapies of the Treatment of Lung Cancer," J. Thorac. Oncol. 3(5):545-555 (2008).
Einhorn, "Perspective on the Development of New Agents in Thoracic Cancers," Lung Cancer 50 Suppl 1:S27-S28 (2005).
Ellis and Crowder, "PIKing" the winner for phosphatidylinositol 3-kinase inhibitors in ErbB2-positive breast cancer: let's not "PTENed" it's easy! Clin. Cancer Res. 13(19):5661-5662 (2007).
Engelman and Settleman, "Acquired Resistance to Tyrosine Kinase Inhibitors During Cancer Therapy," Curr. Opin. Genet. Dev. 18(1):73-79 (2008) (Epub Mar. 5, 2008).
Engelman, "Targeting PI3K Signalling in Cancer: Opportunities, Challenges and Limitations," Nat. Rev. Cancer 9(8):550-562 (2009).
Engleman and Jänne, "Mechanisms of acquired resistance to epidermal growth factor receptor tyrosine kinase inhibitors in non-small cell lung cancer," Clin. Cancer Res. 14(10):2895-2899 (2008).
English Translation of an Opposition filed against corresponding Ecuador Patent Application No. SP-08-8423 in 2008.
Ercan et al., "Amplification of EGFR T790M causes resistance to an irreversible EGFR inhibitor," Oncogene. 29(16):2346-2356 (2010) (Epub Feb. 1, 2010).
Esteva et al., "Molecular predictors of response to trastuzumab and lapatinib in breast cancer," Nat. Rev. Clin. Oncol. 7(2):98-107 (2010) (Epub Dec. 22, 2009).
Ettinger et al., "Antiemesis," J. Natl. Compr. Canc. Netw. 10(4):456-485 (2012).
Farley and Birrer, "Novel Therapeutic Targets," Cancer Treat. Res.149:63-84 (2009).
Felip et al., "Emerging Drugs for Non-Small-Cell Lung Cancer," Expert Opin. Emerg. Drugs 12(3):449-460 (2007).
Ferron et al., "Oral bioavailability of pantoprazole suspended in sodium bicarbonate solution," Am. J. Health Syst. Pharm. 60(13):1324-1329 (2003).
Fertéet al., "Molecular circuits of solid tumors: prognostic and predictive tools for bedside use," Nat. Rev. Clin. Oncol. 7(7):367-380 (2010) (Epub Jun. 15, 2010).
Fitch et al., "Genetics of dark skin in mice," Genes Dev. 17(2):214-228 (2003).
Fleming et al., "Nitrile-containing pharmaceuticals: efficacious roles of the nitrile pharmacophore," J. Med. Chem. 53(22)7902-7917 (2010) (Epub Aug. 30, 2010).
Fleming et al., "Phase II trial of temsirolimus in patients with metastatic breast cancer," Breast Cancer Res. Treat. 136(2):355-363 (2012) (Epub Jan. 13, 2012).
Folkman, "Angiogenesis in cancer, vascular, rheumatoid and other disease," Nat. Med. 1(1):27-31 (1995).
Frederick et al., "Epithelial to mesenchymal transition predicts gefitinib resistance in cell lines of head and neck squamous cell

(56) References Cited

OTHER PUBLICATIONS carcinoma and non-small cell lung carcinoma," Mol. Cancer Ther. 6(6):1683-1691 (2007) (Epub May 31, 2007).
Früh, "The search for improved systemic therapy of non-small cell lung cancer—what are today's options?" Lung Cancer 72(3):265-270 (2011) (Epub Apr. 14, 2011).
Fry, "Inhibition of the epidermal growth factor receptor family of tyrosine kinases as an approach to cancer chemotherapy: progression from reversible to irreversible inhibitors," Pharmacol. Ther. 82(2-3):207-218 (1999).
Fukuoka et al., "Multi-institutional randomized phase II trial of gefitinib for previously treated patients with advanced non-small-cell lung cancer (The IDEAL 1 Trial) [corrected]," J. Clin. Oncol. 21(12):2237-2246 (2003) (Epub May 14, 2003).
Gadji et al., "EGF receptor inhibitors in the treatment of glioblastoma multiform: old clinical allies and newly emerging therapeutic concepts," Eur. J. Pharmacol. 625(1-3):23-30 (2009) (Epub Oct. 18, 2009).
Gajria and Chandarlapaty, "HER2-amplified breast cancer: mechanisms of trastuzumab resistance and novel targeted therapies," Expert Rev. Anticancer Ther. 11(2):263-275 (2011).
Gajria et al., "Tolerability and Efficacy of Targeting Both mTOR and HER2 Signaling in Trastuzumab-Refractory HER2+ Metastatic Breast Cancer," San Antonio Breast cancer Symposium. Abstract P5-18-04 (2010).
Garcia et al., "Promoter Methylation of the PTEN Gene is a Common Molecular Change in Breast Cancer," Genes Chromosomes Cancer 41(2):117-127 (2004).
Garrett and Arteaga, "Resistance to HER2-directed antibodies and tyrosine kinase inhibitors: mechanisms and clinical implications," Cancer Biol. Ther. 11(9):793-800 (2011) (Epub May 1, 2011).
Gatzemeier, "Second-Generation EGFR Inhibitors and Combinations," J. Thorac Oncol. 4(9): S121 (2009).
Gazdar, "Activating and Resistance Mutations of EGFR in Non-Small-Cell Lung Cancer: Role in Clinical Response to EGFR Tyrosine Kinase Inhibitors," Oncogene 28:S24-S31 (2009).
Genentech, Herceptin®-Product Literature, www.Genetech.com, Sep. 1998 Revised (Jun. 2014), pp. 1-35.
Geuna et al., "Hitting multiple targets in HER2-positive breast cancer: proof of principle or therapeutic opportunity?" Expert Opin. Pharmacother. 12(4):549-565 (2011) (Epub Jan. 6, 2011).
Geyer et al., "Lapatinib plus capecitabine for HER2-positive advanced breast cancer," N. Engl. J. Med. 355(26):2733-2743 (2006).
Ghayad and Cohen, "Inhibitors of the PI3K/Akt/mTOR pathway: new hope for breast cancer patients," Recent Pat. Anticancer Drug Discov. 5(1):29-57 (2010).
Giaccone et al., "Gefitinib in combination with gemcitabine and cisplatin in advanced non-small-cell lung cancer: a phase III trial—INTACT 1," J. Clin. Oncol. 22(5):777-784 (2004).
Giamas et al., "Kinases as Targets in the Treatment of Solid Tumors," Cell. Signal. 22(7):984-1002 (2010) (Epub Jan. 21, 2010).
Glaxosmithkline, Tykerb Prescription Label, 2010, pp. 1-25.
Glück, "Chemotherapy Regimens in Metastatic Breast Cancer," Clin. Adv. Hematol. Oncol. 9(1):47-48 (2011).
Godin-Heymann et al., "Oncogenic activity of epidermal growth factor receptor kinase mutant alleles is enhanced by the T790M drug resistance mutation," Cancer Res. 67(15):7319-7326 (2007).
Godin-Heymann et al., "The T790M "gatekeeper" mutation in EGFR mediates resistance to low concentrations of an irreversible EGFR inhibitor," Mol. Cancer Ther. 7(4):874-879 (2008).
Goldhirsch et al., "2 years versus 1 year of adjuvant trastuzumab for HER2-positive breast cancer (HERA): an open-label, randomised control trail," Lancet 382:1021-1028 (2013).
Good, "A Comparison of Contact Angle Interpretations," J. Colloid Interface Sci. 44(1):63-71 (1973).
Govindan, "A review of epidermal growth factor receptor/HER2 inhibitors in the treatment of patients with non-small-cell lung cancer," Clin. Lung Cancer 11(1):8-12 (2010).
Greenberger et al., "EKB-569: a New Irreversible Inhibitor of Epidermal Growth Factor Receptor Tyrosine Kinase for the Treatment of Cancer," Clin. Cancer Res. 6(Suppl):4544s Abstr. 388 (2000).
Greulich et al., "Oncogenic Transformation by Inhibitor-Sensitive and -Resistant EGFR Mutants," PLOS Medicine 2(11) E313:1167-1176 (2005).
Gridelli et al., "Erlotinib in the Treatment of Non-small Cell Lung Cancer: Current Status and Future Developments," Anticancer Res. 30:1301-1310 (2010).
Grimm et al., "Diagnostic and Therapeutic Use of Membrane Proteins in Cancer Cells," Curr. Med. Chem. 18(2):176-190 (2011).
Guarneri et al., "Anti-HER2 neoadjuvant and adjuvant therapies in HER2 positive breast cancer," Cancer Treat. Rev. 36 Suppl 3:S62-S66 (2010).
Guertin et al., "Ablation in mice of the mTORC components raptor, rictor, or mLST8 reveals that mTORC2 is required for signaling to Akt-FOXO and PKCalpha, but not S6K1," Dev. Cell. 11(6):859-871 (2006).
Gullick et al., "Expression of epidermal growth factor receptors on human cervical, ovarian, and vulval carcinomas," Cancer Res. 46(1):285-292 (1986).
Hager et al., "PTEN expression in renal cell carcinoma and oncocytoma and prognosis," Pathology 39(5):482-485 (2007).
Hammerman et al., "Resistance to Epidermal Growth Factor Receptor Tyrosine Kinase Inhibitors in Non-Small Cell Lung Cancer," Clin. Cancer Res. 15(24):7502-7509 (2009).
Harris et al., "c-erbB-2 in serum of patients with breast cancer," Int. J. Biol. Markers 14(1):8-15 (1999).
Hasselblatt, "Ependymal Tumors," Recent Results Cancer Res. 171:51-66 (2009).
Hawkins and Grunberg, "Chemotherapy-Induced Nausea and Vomiting: Challenges and Opportunities for Improved Patient Outcomes," Clin. J. Oncol. Nurs. 13(1):54-64 (2009).
Hegedus et al., "Interaction of ABC multidrug transporters with anticancer protein kinase inhibitors: substrates and/or inhibitors?" Curr. Cancer Drug Targets 9(3):252-272 (2009).
Heigener and Reck, "Mutations in the epidermal growth factor receptor gene in non-small cell lung cancer: Impact on treatment beyond gefitinib and erlotinib," Adv. Ther. 28(2):126-133 (2011) (Epub Dec. 16, 2010).
Heigener, "Non-Small Cell Lung Cancer in Never-Smokers: a New Disease Entity?" Onkologie 34(4):202-207 (2011) (EpubMar. 18, 2011).
Heist et al., "A phase II study of oxaliplatin, pemetrexed, and bevacizumab in previously treated advanced non-small cell lung cancer," J. Thorac. Oncol. 3(10):1153-1158 (2008).
Herbst et al., "Gefitinib in Combination with Paclitaxel and Carboplatin in Advanced Non-Small-Cell Lung Cancer: a Phase III Trial-INTACT 2," J. Clin. Oncol. 22(5):785-794 (2004).
Herbst et al., "Selective oral epidermal growth factor receptor tyrosine kinase inhibitor ZD1839 is generally well-tolerated and has activity in non-small-cell lung cancer and other solid tumors: results of a phase I trial," J. Clin. Oncol. 20(18):3815-3825 (2002).
Heymach et al., "Epidermal growth factor receptor inhibitors in development for the treatment of non-small cell lung cancer," Clin. Cancer Res. 12(14 Pt 2):4441s-4445s (2006).
Higa et al., "Biological considerations and clinical applications of new HER2-targeted agents," Expert Rev. Anticancer Ther. 10(9):1497-1509 (2010).
Ho and Laskin, "EGFR-directed therapies to treat non-small-cell lung cancer," Expert Opin. Investig. Drugs 18(8):1133-1145 (2009).
Holbro and Hynes, "ErbB receptors: directing key signaling networks throughout life," Annu. Rev. Pharmacol. Toxicol. 44:195-217 (2004).
Holodov and Yakovlev, Clinical Pharmacokinetics, Moscow, Medicine, (1985), pp. 83-98, 134-138, 160, 378-380 (English translation not available).
Hookes and Lakeram, "American Chemical Society—235th National Meeting. Part 2: EGFR kinase inhibitors and β3-lactamases under investigation by Wyeth" Idrugs 11(6):391-393 (2008).

(56) References Cited

OTHER PUBLICATIONS

Horn and Sandler, "Epidermal growth factor receptor inhibitors and antiangiogenic agents for the treatment of non-small cell lung cancer," Clin. Cancer Res. 15(16):5040-5048 (2009) (Epub Aug. 11, 2009).
Hou and Kumamoto, "Flavonoids as protein kinase inhibitors for cancer chemoprevention: direct binding and molecular modeling," Antioxid. Redox Signal. 13(5):691-719 (2010).
Huang et al., "Up-regulation of miR-21 by HER2/neu signaling promotes cell invasion," J. Biol. Chem. 284(27):18515-18524 (2009) (Epub May 6, 2009).
Hubalek et al., "Resistance to HER2-targeted therapy: mechanisms of trastuzumab resistance and possible strategies to overcome unresponsiveness to treatment," Wien. Med. Wochenschr. 160(19-20):506-512 (2010) (Epub Oct. 26, 2010).
Huber et al., "Pharmacokinetics of pantoprazole in man," Int. J. Clin. Pharmacol. Ther. 34(5):185-194 (1996).
Hug et al., "A single-dose, crossover, placebo- and moxifloxacin-controlled study to assess the effects of neratinib (HKI-272) on cardiac repolarization in healthy adult subjects," Clin. Cancer Res. 16(15):4016-4023 (2010) (Epub Jul. 20, 2010).
Hung and Lau, "Basic Science of HER-2/neu: a review," Semin Oncol. 26(4 Suppl 12):51-59 (1999).
Hungarian Intellectual Property Office Search Report for Hungarian Patent Application No. 201002712-6 (mailed Aug. 4, 2011).
Hynes and Lane, "ERBB Receptors and Cancer: the Complexity of Targeted Inhibitors," Nat. Rev. Cancer 5(5):341-354 (2005).
ICH Expert Working Group: "Impurities in New Drug Substances Q3A (R2), International Conference on Harmonisation of Technical Requirements for Registration of Pharmaceuticals for Human Use" (Online) 2006.
Ikediobi, "Somatic Pharmacogenomics in Cancer," Pharmacogenomics J. 8(5):305-314 (2008) (Epub Aug. 5, 2008).
Ikezoe et al., "Effect of SU11248 on gastrointestinal stromal tumor-T1 cells: enhancement of growth inhibition via inhibition of 3-kinase/Akt/mammalian target of rapamycin signaling," Cancer Sci. 97(9):945-951 (2006).
Ikezoe et al., "The Anti-Tumor Effects of SU11248, a Class III Receptor Tyrosine Kinase Inhibitor, Against a Variety of Human Hematological Malignancies," Blood (ASH Annual Meeting Abstracts) 106: Abstract 2795 (2005).
Ilango et al., "Investigation of Colon Specificity of Novel Polysaccharide-Okra Mucilage-Film Coated with Enteric Materials," Int. J. Pharma. Bio. Sci. 3(2):52-62 (2012).
Iliadis et al., "APIS: a software for model identification, simulation and dosage regimen calculations in clinical and experimental pharmacokinetics," Computer Methods Programs Biomed. 38(4):227-239 (1992).
International Preliminary Report on Patentability Chapter 1 for International Application No. PCT/US2009/047643 dated Dec. 18, 2010.
International Search Report for International Application No. PCT/US2008/080130, mailed Apr. 5, 2009.
International Search Report for International Patent Application No. PCT/US2009/047643, mailed Jan. 28, 2010.
Isakoff and Baselga, "Trastuzumab-DM1: building a chemotherapy-free road in the treatment of human epidermal growth factor receptor 2-positive breast cancer," J. Clin. Oncol. 29(4):351-354 (2011) (Epub Dec. 20, 2010).
Ito et al., "A Phase 1 Study of Neratinib (HKI-272) in Combination with Paclitaxel in Japanese Patients with Solid Tumors," Ann. Oncol. 21 (Suppl 8):viii103 Abstr. 298P (2010).
Ito et al., "Tolerability and safety of oral neratinib (HKI-272) in Japanese patients with advanced solid tumors," J. Clin. Oncol. 27:(suppl; abstr. e14505) (2009).
Jackisch, "Challenges in the treatment of ErbB2 (HER2)-positive breast cancer," EJC Suppl. 6(5):7-14 (2008).
Jallal et al., "A Src/Abl kinase inhibitor, SKI-606, blocks breast cancer invasion, growth, and metastasis in vitro and in vivo," Cancer Res. 67(4):1580-1588 (2007).

Janczuk and Bialopiotrowicz, "Surface Free-Energy Components of Liquids and Low Energy Solids and Contact Angles," J. Colloid Interface Sci. 127(1):189-204 (1989).
Jänne et al., "Phase I dose-escalation study of the pan-HER inhibitor, PF299804, in patients with advanced malignant solid tumors," Clin. Cancer Res. 17(5):1131-1139 (2011) (Epub Jan. 10, 2011).
Jänne, "Challenges of detecting EGFR T790M in gefitinib/erlotinib-resistant tumours," Lung Cancer 60 Suppl 2:S3-S9 (2008).
Japanese Official Action for Corresponding Japanese Patent Application No. 2010-258729, dated Apr. 12, 2013.
Japanese Official Action mailed Sep. 17, 2013, for Japanese Patent Application No. 2011-289220.
Jasper, "The Surface Tension of Pure Liquid Compounds," J. Phys. Chem. Ref. Data 1:841 (1972).
Jelliffe et al., "Adaptive control of drug dosage regimens: basic foundations, relevant issues, and clinical examples," Int. J. Biomed. Comput. 36(1-2):1-23 (1994).
Ji et al., "Epidermal growth factor receptor variant III mutations in lung tumorigenesis and sensitivity to tyrosine kinase inhibitors," Proc. Natl. Acad. Sci. U.S.A. 103(20):7817-7822 (2006) (Epub May 3, 2006).
Ji et al., "The impact of human EGFR kinase domain mutations on lung tumorigenesis and in vivo sensitivity to EGFR-targeted therapies," Cancer Cell. 9(6):485-495 (2006) (Epub May 25, 2006).
Jimeno and Hidalgo, "Pharmacogenomics of epidermal growth factor receptor (EGFR) tyrosine kinase inhibitors," Biochim Biophys. Acta 1766(2):217-229 (2006) (Epub Sep. 12, 2006).
Johnson et al., "Impact of EGFR mutations on treatment of non-small cell lung cancer," Cancer Chemother. Pharmacol. 58(Suppl1): s5-s9 (2006).
Johnson et al., "Strategies for discovering and derisking covalent, irreversible enzyme inhibitors," Future Med. Chem. 2(6):949-964 (2010).
Johnson, "Biomarkers of Lung Cancer Response to EGFR-TKI," EJC Suppl. 5(8):14-15 Abstr. S23 (2007).
Johnson, "Protein kinase inhibitors: contributions from structure to clinical compounds," Q. Rev. Biophys. 42(1):1-40 (2009) (Epub Mar. 19, 2009).
Jones and Buzdar, "Evolving Novel Anti-HER2 Strategies," Lancet Oncol. 10(12):1179-1187 (2009).
Jones, "Adaptive trials receive boost," Nat. Rev. Drug Discov. 9(5):345-348 (2010) (Epub Apr. 23, 2010).
Jones, "HER4 intracellular domain (4ICD) activity in the developing mammary gland and breast cancer," J. Mammary Gland Biol. Neoplasia 13(2):247-258 (2008) (Epub May 13, 2008).
Jorissen et al., "Epidermal growth factor receptor: mechanisms of activation and signalling," Exp. Cell. Res. 284(1):31-53 (2003).
Joshi and Kucherlapati, "Pharmacogenomics of lung cancer: with a view to address EGFR-targeted therapies," Pharmacogenomics 8(9):1211-1220 (2007).
Kamath and Buolamwini, "Targeting EGFR and HER-2 receptor tyrosine kinases for cancer drug discovery and development," Med. Res. Rev. 26(5):569-594 (2006).
Kane, "Cancer Therapies Targeted to the Epidermal Growth Factor Receptor and Its Family Members," Expert Opin. Ther. Pat. 16(2):147-164 (2006).
Kaplan and Meier, "Nonparametric Estimation From Incomplete Observations," J. Am. Stat. Assoc. 53:457-481 (1958).
Katakami et al., "LUX-Lung 4: a phase II trial of afatinib in patients with advanced non-small-cell lung cancer who progressed during prior treatment with erlotinib, gefitinib, or both," J. Clin. Oncol. 31(27):3335-3341 (2013) (Epub Jul. 1, 2013).
Katzel et al., "Recent advances of novel targeted therapy in non-small cell lung cancer," .J Hematol. Oncool. 2:2 (2009).
Kennedy et al., "Novel Agents in the Management of Lung Cancer," Curr. Med. Chem. 17(35):4291-4325 (2010).
Kim et al., "Chasing targets for EGFR tyrosine kinase inhibitors in non-small-cell lung cancer: Asian perspectives," Expert Rev. Mol. Diagn.7(6):821-836 (2007).
Kim et al., "The role of HER-2 oncoprotein in drug-sensitivity in breast cancer (Review)," Oncol. Rep. 9(1):3-9 (2002).

(56) References Cited

OTHER PUBLICATIONS

Klein and Levitzki, "Targeting the EGFR and the PKB Pathway in Cancer," Curr. Opin. Cell. Biol. 21(2):185-193 (2009) (Epub Feb. 11, 2009).
Klüter et al., "Characterization of irreversible kinase inhibitors by directly detecting covalent bond formation: a tool for dissecting kinase drug resistance," ChemBioChem 11(18):2557-2566 (2010).
Kobayashi et al., "EGFR mutation and resistance of non-small-cell lung cancer to gefitinib," N. Engl. J. Med. 352(8):786-792 (2005).
Kotteas et al., "Targeted therapy for nonsmall cell lung cancer: focusing on angiogenesis, the epidermal growth factor receptor and multikinase inhibitors," Anticancer Drugs 21(2):151-168 (2010).
Kris et al., "Efficacy of gefitinib, an inhibitor of the epidermal growth factor receptor tyrosine kinase, in symptomatic patients with non-small cell lung cancer: a randomized trial," JAMA 290(16):2149-2158 (2003).
Krop, "Managing Trastuzumab-resistant Breast Cancer," Clin. Adv. Hematol. Oncol. 7(2):108-110 (2009).
Kulke et al., "Capecitabine Plus Erlotinib in Gemcitabine-Refractory Advanced Pancreatic Cancer," J. Clin. Oncol. 25(30):4787-4792 (2007).
Kuznar, "New Small Molecule Added to Trastuzumab Improves Survival in Metastatic Disease," Am. Health Drug Benefits 2(5):27 (2009).
Kwak et al., "Irreversible inhibitors of the EGF receptor may circumvent acquired resistance to gefitinib," Proc. Natl. Acad. Sci. U.S.A. 102(21):7665-7670 (2005) (Epub May 16, 2005).
La Motta et al., "Computational studies of epidermal growth factor receptor: docking reliability, three-dimensional quantitative structure-activity relationship analysis, and virtual screening studies," J. Med. Chem. 52(4):964-975 (2009).
Laack et al., "Lessons learnt from gefitinib and erlotinib: Key insights into small-molecule EGFR-targeted kinase inhibitors in non-small cell lung cancer," Lung Cancer 69(3):259-264 (2010) (Epub Jun. 19, 2010).
Lam and Mok, "Targeted Therapy: An Evolving World of Lung Cancer," Respirology 16(1):13-21 (2011) (Epub Aug. 16, 2010).
Langdon et al., "Pertuzumab—Humanized anti-HER2 monoclonal antibody HER dimerization inhibitor oncolytic," Drugs Future 33(2):123-130 (2008).
Langer and Soria, "The role of anti-epidermal growth factor receptor and anti-vascular endothelial growth factor therapies in the treatment of non-small-cell lung cancer," Clin. Lung Cancer 11(2):82-90 (2010).
Lapatinib and Vinorelbine in Treating Patients with Advanced Solid Tumors, clinicaltrials.gov, [Online], U.S. National Institutes of Health, May 26, 2008, [Retrieved on Aug. 30, H-25 (2013)], obtained from the Internet, URL, http://clinicaltrials.gov/archive/NCT00389922/2008_05_26.
Lapatinib and Vinorelbine in Treating Women With HER2-Overexpressing Locally Advanced or Metastatic Breast Cancer, http://clinicaltrials.gov, [Online], U.S. National Institutes of Health, May 26, 2008, [Retrieved on Aug. 30, H-25 (2013)], obtained from the Internet, URL, http://clinicaltrials.gov/archive/NCT00513058/2008_05_26.
Lee et al., "Lung Cancer in Never Smokers: Change of a Mindset in the Molecular Era," Lung Cancer 72(1):9-15 (2011) (Epub Jan. 26, 2011).
Lee et al., "Phase II Study of Vinorelbine Plus Trastuzumab in HER2 Overexpressing Metastatic Breast Cancer Pretreated with Anthracyclines and Taxanes," J. Breast Cancer 14(2):140-146 (2011).
Leone and Dudek, "Enzyme replacement therapy for Gaucher's disease in patient treated for non-small cell lung cancer," Anticancer Res. 28(6B):3937-3939 (2008).
Levitzki and Mishani, "Tyrphostins and other tyrosine kinase inhibitors," Annu Rev. Biochem. 75:93-109 (2006).
Li and Perez-Soler, "Skin toxicities associated with epidermal growth factor receptor inhibitors," Target. Oncol. 4(2):107-119 (2009) (Epub May 19, 2009).
Li and Sun, "PTEN/MMAC1/TEP1 suppresses the tumorigenicity and induces G1 cell cycle arrest in human glioblastoma cells," Proc. Natl. Acad. Sci. U.S.A. 95(26):15406-15411 (1998).
Li and Sun, "TEP1, encoded by a candidate tumor suppressor locus, is a novel protein tyrosine phosphatase regulated by transforming growth factorβ," Cancer Res. 57(11):2124-2129 (1997).
Li et al., "BIBW2992, an irreversible EGFR/HER2 inhibitor highly effective in preclinical lung cancer models," Oncogene 27(34):4702-4711 (2008) (Epub Apr. 14, 2008).
Li et al., "Bronchial and peripheral murine lung carcinomas induced by T790M-L858R mutant EGFR respond to HKI-272 and rapamycin combination therapy," Cancer Cell 12(1):81-93 (2007).
Li et al., "PTEN, a putative protein tyrosine phosphatase gene mutated in human brain, breast, and prostate cancer," Science 275(5308):1943-1947 (1997).
Ligibel and Winer, "Trastuzumab/chemotherapy combinations in metastatic breast cancer," Semin. Oncol. 29(3 Suppl 11):38-43 (2002).
Limentani et al., "Safety and Efficacy of Neratinib (HKI-272) in Combination with Vinorelbine in Patients with Solid Tumors," J. Clin. Oncol. (Meeting Abstracts) 27(15S):e14554 (2009).
Lin and Winer, "Chemotherapy agents in human epidermal growth factor receptor 2-positive breast cancer: time to step out of the limelight," J. Clin. Oncol. 29(3):251-253 (2011) (Epub Dec. 13, 2010).
Lin and Yang, "Epidermal growth factor receptor tyrosine kinase inhibitors in elderly or poor performance status patients with advanced non-small cell lung cancer," Target. Oncol. 4(1):37-44 (2009) (Epub Jan. 20, 2009).
Linardou et al., "Somatic EGFR mutations and efficacy of tyrosine kinase inhibitors in NSCLC," Nat. Rev. Clin. Oncol. 6(6):352-366 (2009).
Little, "Molecular Tests, Targets and Therapies for Cancer," EPC (DIA 43rd Annual Meeting Edition) p. 98 (2007).
Liu et al., "Targeting epidermal growth factor receptor in lung cancer: Perspective from the Asia—Pacific region," Asia-Pac. J. Clin. Oncol. 2:22-31 (2006).
Locker et al., "ASCO 2006 update of recommendations for the use of tumor markers in gastrointestinal cancer," J. Clin. Oncol. 24(33):5313-5327 (2006) (Epub Oct. 23, 2006).
Loew et al., "The epidermal growth factor receptor as a therapeutic target in glioblastoma multiforme and other malignant neoplasms," Anticancer Agents Med. Chem. 9(6):703-715 (2009).
Loke, "Drug-drug interactions—bridging the gulf between the bench and the bedside?" Br. J. Clin. Pharmacol. 71(4):485-486 (2011).
LoPiccolo et al., "Targeting the PI3K/Akt/mTOR pathway: effective combinations and clinical considerations," Drug Resist. Updat. 11(1-2):32-50 (2008) (Epub Dec. 31, 2007).
Loriot et al., "Drug insight: gastrointestinal and hepatic adverse effects of molecular-targeted agents in cancer therapy," Nat. Clin. Pract. Oncol. 5(5):268-278 (2008) (Epub Mar. 18, 2008).
Loriot et al., "Pemetrexed-induced pneumonitis: a case report," Clin. Lung Cancer 10(5):364-366 (2009).
Lorusso and Eder, "Therapeutic potential of novel selective-spectrum kinase inhibitors in oncology," Expert Opin. Investig. Drugs 17(7):1013-1028 (2008).
Lou et al., "Progress in Target Therapy for Breast Cancer," J. Oncology 15(9):788-795 (2009). (English Abstract).
Lu and Ku, "Preformulation stability study of the EGFR inhibitor HKI-272 (Neratinib) and mechanism of degradation," Drug Dev. Ind. Pharm. 1-7 (2011).
Lu et al., "The PTEN/MMAC1/TEP tumor suppressor gene decreases cell growth and induces apoptosis and anoikis in breast cancer cells," Oncogene 18(50):7034-7045 (1999).
Luetteke et al., "The mouse waved-2 phenotype results from a point mutation in the EGF receptor tyrosine kinase," Genes Dev. 8(4):399-413 (1994).
Lynch et al., "Activating mutations in the epidermal growth factor receptor underlying responsiveness of non-small-cell lung cancer to gefitinib," N. Engl. J. Med. 350(21):2129-2139 (2004) (Epub Apr. 29, 2004).

(56) References Cited

OTHER PUBLICATIONS

Lynch et al., "Novel Agents in the Treatment of Lung Cancer: Fourth Cambridge Conference," Clin. Cancer Res. 13(15 Suppl.):4583s-4588s (2007).
Lynch et al., "Summary statement novel agents in the treatment of lung cancer: Fifth Cambridge Conference assessing opportunities for combination therapy," J. Thorac. Oncol. 3(6 Suppl 2):S107-S112 (2008).
Lynch, "Molecular Staging of NSCLC: 2006," EJC (Suppl 4):24-25 Abstr. S55 (2006).
Ma et al., "PIK3CA as an oncogene in cervical cancer," Oncogene 19(23):2739-2744 (2000).
Macrinici and Romond, "Clinical updates on EGFR/HER targeted agents in early-stage breast cancer," Clin. Breast Cancer 10 Suppl 1:E38-E46 (2010).
Maehama et al., "A sensitive assay for phosphoinositide phosphatases," Anal Biochem. 279(2):248-250 (2000).
Maehama et al., "PTEN and myotubularin: novel phosphoinositide phosphatases," Annu. Rev. Biochem. 70:247-279 (2001).
Maehama, "PTEN: its deregulation and tumorigenesis," Biol. Pharm. Bull. 30(9):1624-1627 (2007).
Mallon et al., "Antitumor efficacy of PKI-587, a highly potent dual PI3K/mTOR kinase inhibitor," Clin. Cancer Res. 17(10):3193-3203 (2011) (Epub Feb. 15, 2011).
Man et al., "New and established targets for the treatment of breast cancer," Adv. Breast Cancer 7(3):10-13 (2010).
Mantel and Haenszel, "Statistical aspects of the analysis of data from retrospective studies of disease," J. Natl. Cancer Inst. 22(4):719-748 (1959).
Martinez-Garcia et al., "Tyrosine Kinase Inhibitors in Breast Cancer: Present Status and Perspectives," Cancer Chemother. Rev. 186-194 (2010).
Mattsson and Clowes, "Current concepts in restenosis following balloon angioplasty," Trends Cardiovasc. Med. 5(5):200-204 (1995).
Mauriz and Gonzalez-Gallego, "Antiangiogenic drugs: current knowledge and new approaches to cancer therapy," J. Pharm. Sci. 97(10):4129-4154 (2008).
Mayer, "Treatment of HER2-positive metastatic breast cancer following initial progression," Clin. Breast Cancer 9 Suppl 2:S50-S57 (2009).
McDermott et al., "Acquired resistance of non-small cell lung cancer cells to MET kinase inhibition is mediated by a switch to epidermal growth factor receptor dependency," Cancer Res. 70(4):1625-1634 (2010) (Epub Feb. 2, 2010).
McDermott et al., "High-throughput lung cancer cell line screening for genotype-correlated sensitivity to an EGFR kinase inhibitor," Methods Enzymol. 438:331-341 (2008).
McDermott et al., "Identification of genotype-correlated sensitivity to selective kinase inhibitors by using high-throughput tumor cell line profiling," Proc. Natl. Acad. Sci. U.S.A. 104(50):19936-19941 (2007) (Epub Dec. 6, 2007).
Mehta and Osipo, "Trastuzumab resistance: role for Notch signaling," ScientificWorldJournal 9:1438-1448 (2009).
Mendelsohn and Baselga, "The EGF receptor family as targets for cancer therapy," Oncogene 19(56):6550-6565 (2000).
Mendoza, "Targeted therapies in the treatment of advanced non-small-cell lung cancer: update," Klin.Onkol. 22(4):131-138 (2009).
Meng et al., "MicroRNA-21 regulates expression of the PTEN tumor suppressor gene in human hepatocellular cancer," Gastroenterology 133(2):647-658 (2007) (Epub May 21, 2007).
Metro and Cappuzzo, "New targeted therapies for non-small-cell lung cancer," Therapy 6(3):335-350 (2009).
Metzger-Filho et al., "Management of metastatic HER2-positive breast cancer progression after adjuvant trastuzumab therapy—current evidence and future trends," Expert Opin. Investig. Drugs 19 Suppl 1:S31-S39 (2010).
Metzger-Filho et al., "Molecular targeted therapy in prevalent tumors: learning from the past and future perspectives," Current Clin. Pharmacol. 5(3):166-177 (2010).
Meyerhardt et al., "Phase II study of capecitabine, oxaliplatin, and erlotinib in previously treated patients with metastastic colorectal cancer," J. Clin. Oncol. 24(12):1892-1897 (2006).
Minami et al., "The major lung cancer-derived mutants of ERBB2 are oncogenic and are associated with sensitivity to the irreversible EGFR/ERBB2 inhibitor HKI-272," Oncogene 26(34):5023-5027 (2007) (Epub Feb. 19, 2007).
Minkovsky and Berezov, "BIBW-2992, a dual receptor tyrosine kinase inhibitor for the treatment of solid tumors," Curr. Opin. Investig. Drugs 9(12):1336-1346 (2008).
Mitsudomi et al., "Biological and clinical implications of EGFR mutations in lung cancer," Int. J. Clin. Oncol. 11(3):190-198 (2006).
Moasser, "Targeting the function of the HER2 oncogene in human cancer therapeutics," Oncogene 26(46):6577-6592 (2007) (Epub May 7, 2007).
Morabito et al., "Methodological Issues of Clinical Research with EGFR Inhibitors," Curr. Cancer Ther. Rev. 3(4):292-302 (2007).
Moreno-Aspitia and Perez, "Treatment options for breast cancer resistant to anthracycline and taxane," Mayo Clin. Proc. 84(6):533-545 (2009).
Morozova et al., "System-level analysis of neuroblastoma tumor-initiating cells implicates AURKB as a novel drug target for neuroblastoma," Clin. Cancer Res. 16(18):4572-4582 (2010) (Epub Jul. 22, 2010).
Morris and Hudis, "Personalizing therapy for metastatic breast cancer," Expert Rev. Anticancer Ther. 9(9):1223-1226 (2009).
Morrow et al., "Recent advances in systemic therapy: Advances in systemic therapy for HER2-positive metastatic breast cancer," Breast Cancer Res. 11(4):207 (2009) (Epub Jul. 15, 2009).
Mukai, "Targeted therapy in breast cancer: current status and future directions," Jpn. J. Clin. Oncol. 40(8):711-716 (2010) (Epub Apr. 8, 2010).
Mukai, "Treatment strategy for HER2-positive breast cancer," Int. J. Clin. Oncol. 15(4):335-340 (2010) (Epub Jul. 15, 2010).
Mukherji and Spicer, "Second-generation epidermal growth factor tyrosine kinase inhibitors in non-small cell lung cancer," Expert Opin. Investig. Drugs 18(3):293-301 (2009).
Mullard, "2010 in Reflection," Nat. Rev. Drug Discov. 10:7-9 (2011).
Munagala et al., "Promising molecular targeted therapies in breast cancer," Indian J Pharmacol. 43(3):236-245 (2011).
Mundhenke et al., "Significance of Tyrosine Kinase Inhibitors in the Treatment of Metastatic Breast Cancer," Breast Care (Basel) 4(6):373-378 (2009) (Epub Nov. 16, 2009).
Murphy and Fornier, "HER2-positive breast cancer: beyond trastuzumab," Oncology (Williston Park) 24(5):410-415 (2010).
Muthuswamy, "Trastuzumab resistance: all roads lead to SRC," Nat. Med. 17(4):416-418 (2011).
Nagata et al., "PTEN activation contributes to tumor inhibition by trastuzumab, and loss of PTEN predicts trastuzumab resistance in patients," Cancer Cell vol. 6(2):117-127 (2004).
Nahta and O'Regan, "Evolving strategies for overcoming resistance to HER2-directed therapy: targeting the PI3K/Akt/mTOR pathway," Clin. Breast Cancer 10 Suppl 3:S72-S78 (2010).
Nakagawa et al., "Combined therapy with mutant-selective EGFR inhibitor and Met kinase inhibitor for overcoming erlotinib resistance in EGFR-mutant lung cancer," 11(10):2149-2157 (2012) (Epub Jul. 25, 2012).
Natoli et al., "Tyrosine kinase inhibitors," Curr. Cancer Drug Targets 10(5):462-483 (2010).
Nguyen et al., "Acquired resistance to epidermal growth factor receptor tyrosine kinase inhibitors in non-small-cell lung cancers dependent on the epidermal growth factor receptor pathway," Clin. Lung Cancer 10(4):281-289 (2009).
Nicholson et al., "EGFR and cancer prognosis," Eur. J. Cancer 37 Suppl 4:S9-S15 (2001).
Nielsen et al., "HER2-targeted therapy in breast cancer. Monoclonal antibodies and tyrosine kinase inhibitors," Cancer Treat Rev. 35(2):121-136 (2009) (Epub Nov. 12, 2008).
Nitz, "Perspectives: Other ErbB2-Targeted Therapies," Breast Care (Basel) 5(s1):25-27 (2010) (Epub Apr. 26, 2010).

(56) References Cited

OTHER PUBLICATIONS

Nolé et al., "Dose-finding and pharmacokinetic study of an all-oral combination regimen of oral vinorelbine and capecitabine for patients with metastatic breast cancer," Ann. Oncol. 17(2):322-329 (2006) (Epub Nov. 22, 2005).
O'Brien et al., "Activated phosphoinositide 3-kinase/AKT signaling confers resistance to trastuzumab but not lapatinib," Mol. Cancer Ther. 9(6):1489-1502 (2010) (Epub May 25, 2010).
Ocaña and Amir, "Irreversible pan-ErbB tyrosine kinase inhibitors and breast cancer: current status and future directions," Cancer Treat. Rev. 35(8):685-691 (2009) (Epub Sep. 4, 2009).
Ocaña and Pandiella, "Identifying breast cancer druggable oncogenic alterations: lessons learned and future targeted options," Clin. Cancer Res. 14(4):961-970 (2008).
Ocaña et al., "New Targeted Therapies in Head and Neck Cancer," Cancer Chemo. Rev. 4:35-43 (2009).
Ocaña et al., "Novel tyrosine kinase inhibitors in the treatment of cancer," Curr. Drug Targets 10(6):575-576 (2009).
Ocaña et al., "Preclinical development of molecular-targeted agents for cancer," Nat. Rev. Clin. Oncol. 8:200-209 (2011).
Office Action dated May 26, 2010 issued in corresponding European Patent Application No. 06836862.0.
Office Action dated Oct. 28, 2013 issued in corresponding Japanese Patent Application No. 2012-179873.
Office Action issued in corresponding Pakistan Patent Application No. 1456/2006 in 2007.
Official Action and Search Report with English Translation, dated Jun. 18, 2013, for corresponding Chinese Application No. 201210328133.2.
Official Action from corresponding Japanese Application JP 2012-279650, mailed Apr. 22, 2014 [along with an English Translation, received Jul. 16, 2014].
Oh et al., "Detection of epidermal growth factor receptor in the serum of patients with cervical carcinoma," Clin. Cancer Res. 6(12):4760-4763 (2000).
O'Hare et al., "Bcr-Abl kinase domain mutations and the unsettled problem of Bcr-AblT315I: looking into the future of controlling drug resistance in chronic myeloid leukemia," Clin. Lymphoma Myeloma 7 Suppl 3:S120-S130 (2007).
Okumura et al., "Induction of Noxa Sensitizes Human Colorectal Cancer Cells Expressing Mcl-1 to the Small-Molecule Bcl-2/Bcl-$x_L$ Inhibitor, ABT-737," Clin. Cancer Res. 14(24):8132-8142 (2008).
Omuro et al., "Lessons learned in the development of targeted therapy for malignant gliomas," Mol. Cancer Ther. 6(7):1909-1919 (2007).
O'Neil et al., (ed.). The Merck Index—An Encyclopedia of Chemicals, Drugs, and Biologicals. 13th Edition, Whitehouse Station, NJ: Merck and Co., Inc., 2001., p. 1454-1455.
Oshima, "Crystallization of Polymorphs and Pseudo-Polymorphs and Its Control," Pharm. Stage 6(10):48-53 (2007). [English Translation Not Available].
Ouchi et al., "Antitumor activity of erlotinib in combination with capecitabine in human tumor xenograft models," Cancer Chemother. Pharmacol. 57(5):693-702 (2006).
Pal et al., "Targeted therapies for non-small cell lung cancer: an evolving landscape," Mol. Cancer Ther. 9(7):1931-1944 (2010) (Epub Jun. 22, 2010).
Pallis et al., "Targeted therapies in the treatment of advanced/metastatic NSCLC," Eur. J. Cancer 45(14):2473-2487 (2009).
Pantuck et al., "Prognostic relevance of the mTOR pathway in renal cell carcinoma: implications for molecular patient selection for targeted therapy," Cancer 109(11):2257-2267 (2007).
Pao and Chmielecki, "Rational, biologically based treatment of EGFR-mutant non-small-cell lung cancer," Nat. Rev. Cancer 10(11):760-774 (2010) (Epub Oct. 22, 2010).
Pao, "Defining clinically relevant molecular subsets of lung cancer," Cancer Chemother. Pharmacol. 58(Suppl 1):s11-s15 (2006).
Papaldo et al., "A phase II study on metastatic breast cancer patients treated with weekly vinorelbine with or without trastuzumab according to HER2 expression: changing the natural history of HER2-positive disease," Ann. Oncol. 17(4):630-636 (2006) (Epub Jan. 12, 2006).
Paridaens et al., "Neratinib (HKI-272), an irreversible pan-ErbB receptor tyrosine kinase inhibitor: Phase 2 results in patients with ErbB2+ advanced breast cancer," Ann. Oncol. 20(Suppl 2):ii61-ii62 Abstr. 186P (2009).
Parkin and Fernández, "Use of statistics to assess the global burden of breast cancer," Breast J. 12(Suppl 1):S70-S80 (2006).
Pegram et al., "Expert roundtable: emerging questions in ErbB2-positive breast cancer; Feb. 22, 2007," Clin. Breast Cancer 8(Suppl 3):S131-S141 (2008).
Pegram et al., "The molecular and cellular biology of HER2/neu gene amplification/overexpression and the clinical development of herceptin (trastuzumab) therapy for breast cancer," Cancer Treat. Res. 103:57-75 (2000).
Perez et al., "Updated Results of the Combined Analysis of NCCTG N9831 and NSABP B-31 Adjuvant Chemotherapy With/Without Trastuzumab in Patients with HER2-Positive Breast Cancer," J. Clin. Oncol. ASCO Annual Meeting Proc. 25(18S):512 (2007).
Pérez-Soler, "Individualized therapy in non-small-cell lung cancer: future versus current clinical practice," Oncogene 28(Suppl 1):S38-S45 (2009).
Pérez-Tenorio et al., "PIK3CA mutations and PTEN loss correlate with similar prognostic factors and are not mutually exclusive in breast cancer," Clin. Cancer Res. 13(12):3577-3584 (2007).
Perren et al., "Immunohistochemical evidence of loss of PTEN expression in primary ductal adenocarcinomas of the breast," Am. J. Pathol. 155(4):1253-1260 (1999).
Petter et al., "A novel small-molecule drug platform to silence cancer targets—application to the panEibB kinases," In: Proceedings of the 100th Annual Meeting of the American Association for Cancer Research; Apr. 18-22, 2009; Denver, CO. Abstr. 3746 (2009).
Pfister et al., "American Society of Clinical Oncology Clinical Practice Guideline for the Use of Larynx-Preservation Strategies in the Treatment of Laryngeal Cancer," J. Clin. Oncol. 24(22):3693-3704 (2006) (Epub Jul. 10, 2006).
Piccart et al., "Beyond trastuzumab: new anti-HER2 agents," Breast 20(Suppl 1):S1-S2 Abstr. S02 (2011).
Piccart, "Circumventing de novo and acquired resistance to trastuzumab. new hope for the care of ErbB2-positive breast cancer," Clin. Breast Cancer 8(Suppl 3):S100-S113 (2008).
Plati et al., "Dysregulation of apoptotic signaling in cancer: molecular mechanisms and therapeutic opportunities," J. Cell. Biochem. 104(4):1124-1149 (2008).
Plosker and Keam, "Trastuzumab: a review of its use in the management of HER2-positive metastatic and early-stage breast cancer," Drugs 66(4):449-475 (2006).
Ponz-Sarvisé et al., "Epidermal growth factor receptor inhibitors in colorectal cancer treatment: what's new?" World J. Gastroenterol. 13(44):5877-5887 (2007).
Potashman and Duggan, "Covalent modifiers: an orthogonal approach to drug design," J. Med. Chem. 52(5):1231-1246 (2009).
Rabindran, "Antitumor activity of HER-2 inhibitors," Cancer Lett. 227(1):9-23 (2005) (Epub Dec. 15, 2004).
Raines and Ross, "Multiple growth factors are associated with lesions of atherosclerosis: specificity or redundancy?" Bioessays 18(4):271-282 (1996).
Rampaul et al., "Clinical value of epidermal growth factor receptor expression in primary breast cancer," Adv. Anat. Pathol. 12(5):271-273 (2005).
Rana and Swaby, "Targeted Therapies for HER2 Breast Cancer: A View of the Landscape," Curr. Breast Cancer Rep. 3:55-62 (2011).
Ranganathan and Muneer, "Highlights from: The 24th Annual Meeting of the American Association for Cancer Research; Los Angeles, CA; Apr. 14-18, 2007," Clin. Lung Cancer 8(6):359-363 (2007).
Ray et al., "Lung cancer therapeutics that target signaling pathways: an update," Expert Rev. Respir. Med. 4(5):631-645 (2010).
Ray et al., "The role of EGFR inhibition in the treatment of non-small cell lung cancer," Oncologist 14(11):1116-1130 (2009) (Epub Nov. 5, 2009).

(56) References Cited

OTHER PUBLICATIONS

Redon et al., "A simple specific pattern of chromosomal aberrations at early stages of head and neck squamous cell carcinomas. PIK3CA but not p63 gene as a likely target of 3q26-qter gains," Cancer Res. 61(10):4122-4129 (2001).
Reid et al., "Dual inhibition of ErbB1 (EGFR/HER1) and ErbB2 (HER2/neu)," Eur. J. Cancer 43(3):481-489 (2007) (Epub Jan. 8, 2007).
Response filed by Applicant on Apr. 30, 2009 to Office Action dated Jul. 18, 2008, in corresponding European Patent Application No. 06836862.0.
Rewcastle et al., "Synthesis of 4-(phenylamino)pyrimidine derivatives as ATP-competitive protein kinase inhibitors with potential for cancer chemotherapy," Curr. Org. Chem. 4(7):679-706 (2000).
Rexer et al., "Overcoming resistance to tyrosine kinase inhibitors: lessons learned from cancer cells treated with EGFR antagonists," Cell Cycle 8(1):18-22 (2009) (Epub Jan. 30, 2009).
Rich et al., "Phase II trial of gefitinib in recurrent glioblastoma," J. Clin. Oncol. 22(1):133-142 (2004) (Epub Nov. 24, 2003).
Riely et al., "Update on epidermal growth factor receptor mutations in non-small cell lung cancer," Clin. Cancer Res. 12(24):7232-7241 (2006).
Riely, "Second-generation epidermal growth factor receptor tyrosine kinase inhibitors in non-small cell lung cancer," J. Thorac. Oncol. 3(6 Suppl 2):S146-S149 (2008).
Rosell et al., "Age-related genetic abnormalities: the Achilles' heel for customizing therapy in elderly lung cancer patients," Personalized Medicine 4(1):59-72 (2007).
Rosell et al., "Screening for epidermal growth factor receptor mutations in lung cancer," N. Engl. J. Med. 361(10):958-967 (2009) (Epub Aug. 19, 2009).
Rosell et al., "Treatment of non-small-cell lung cancer and pharmacogenomics: where we are and where we are going," Curr. Opin. Oncol. 18(2):135-143 (2006).
Rosen et al., "Targeting signal transduction pathways in metastatic breast cancer: a comprehensive review," Oncologist 15(3):216-235 (2010) (Epub Mar. 3, 2010).
Ross et al., "The HER-2 receptor and breast cancer: ten years of targeted anti-HER-2 therapy and personalized medicine," Oncologist 14:320-368 (2009).
Rotella, "Medicinal Chemistry—XXth International Symposium. Lead finding strategies and kinase selectivity," IDrugs 11(11):774-778 (2008).
Roukos, "Trastuzumab and beyond: sequencing cancer genomes and predicting molecular networks," Pharmacogenomics J. 11(2):81-92 (2011) (Epub Oct. 26, 2010).
Roy and Perez, "Beyond trastuzumab: small molecule tyrosine kinase inhibitors in HER-2-positive breast cancer," Oncologist 14(11):1061-1069 (2009) (Epub Nov. 3, 2009).
Rubin et al., "10q23.3 loss of heterozygosity is higher in lymph node-positive (pT2-3,N+) versus lymph node-negative (pT2-3,N0) prostate cancer," Hum. Pathol. 31(4):504-508 (2000).
Rudloff and Samuels, "A growing family: adding mutated Erbb4 as a novel cancer target," Cell Cycle. 9(8):1487-1503 (2010) (Epub Apr. 15, 2010).
Saal et al., "PIK3CA mutations correlate with hormone receptors, node metastasis, and ERBB2, and are mutually exclusive with PTEN loss in human breast carcinoma," Cancer Res. 65(7):2554-2559 (2005).
Sakamoto et al., "Su-11248 Sugen," Curr. Opin. Investig. Drugs 5(12):1329-1339 (2004).
Salvesen et al., "Integrated genomic profiling of endometrial carcinoma associates aggressive tumors with indicators of PI3 kinase activation," Proc. Natl. Acad. Sci. U.S.A. 106(12):4834-4839 (2009) (Epub Mar. 4, 2009).
Samuels and Ericson, "Oncogenic PI3K and its role in cancer," Curr. Opin. Oncol. 18(1):77-82 (2006).
Sanchez-Martin and Pandiella, "Differential action of ErbB kinase inhibitors on receptor oligomerization," EJC Suppl. 8:107 Abstr. 337 (2010).
Santarpia et al., "Tyrosine kinase inhibitors for non-small-cell lung cancer: finding patients who will be responsive," Expert Rev. Respir. Med. (3):413-424 (2011).
Sartore-Bianchi et al., "Rationale and clinical results of multi-target treatments in oncology," Int. J. Biol. Markers 22(1 Suppl 4):S77-S87 (2007).
Sathornsumetee et al., "Malignant glioma drug discovery—targeting protein kinases," Expert Opin. Drug Discov. 2(1):1-17 (2007).
Sattler et al., "EGFR-targeted therapeutics: focus on SCCHN and NSCLC," ScientificWorldJournal 8:909-919 (2008).
Saura et al., "Safety of Neratinib (HKI-272) in Combination with Capecitabine in Patients with Solid Tumors: A Phase 1/2 Study," Cancer Res. 69(24 Suppl) Abstr. 5108 (2009).
Saura et al., "The safety of Neratinib (HKI-272) in Combination with Capecitabine in Patients with Solid Tumors: A Phase 1/2 Study," Ann. Oncol. 21(Suppl 4):iv63 Abstr. 147P (2010).
Saura et al., (Dec. 2011). Safety and Efficacy of Neratinib in Combination with Capecitabine in Patients with ErbB2-Positive Breast Cancer. Poster presented at the 2011 CTRC-AACR San Antonio Breast Cancer Symposium, San Antonio, Texas.
Scaltriti et al., "Expression of p95HER2, a truncated form of the HER2 receptor, and response to anti-HER2 therapies in breast cancer," J. Natl. Cancer Inst. 99(8):628-638 (2007).
Schiller et al., "Comparison of four chemotherapy regimens for advanced non-small-cell lung cancer," N. Engl. J. Med. 346(2):92-98 (2002).
Scott and Salgia, "Biomarkers in lung cancer: from early detection to novel therapeutics and decision making," Biomark. Med. 2(6):577-586 (2008).
Sebastian et al., "The complexity of targeting EGFR signalling in cancer: from expression to turnover," Biochim Biophys. Acta. 1766(1):120-139(2006) (Epub Jun. 23, 2006).
Sequist and Dziadziuszko, "Update on epidermal growth factor receptor inhibitor development in lung cancer," J. Thorac. Oncol. 1(7):740-743 (2006).
Sequist et al., "Neratinib, an irreversible pan-ErbB receptor tyrosine kinase inhibitor: results of a phase II trial in patients with advanced non-small-cell lung cancer," J. Clin. Oncol. 28(18):3076-3083 (2010) (Epub May 17, 2010).
Sequist, "Second-generation epidermal growth factor receptor tyrosine kinase inhibitors in non-small cell lung cancer," Oncologist 12(3):325-330 (2007).
Settleman and Kurie, "Drugging the bad "AKT-TOR" to overcome TKI-resistant lung cancer," Cancer Cell 12(1):6-8 (2007).
Seyhan et al., "A genome-wide RNAi screen identifies novel targets of neratinib sensitivity leading to neratinib and paclitaxel combination drug treatments," Mol. Biosyst. 7(6):1974-1989 (2011) (Epub Apr. 12, 2011).
Sharma and Jayanth, "Neratinib, an irreversible erbB receptor tyrosine Kinase inhibitor, in patients with advanced erbB2-positive breast cancer," [commentary] Adv. Breast Cancer 7(1):21 (2010).
Sharma and Settleman, "Oncogene addiction: setting the stage for molecularly targeted cancer therapy," Genes Dev. 21(24):3214-3231 (2007).
Sharma et al., "Epidermal growth factor receptor mutations in lung cancer," Nat. Rev. Cancer7(3):169-181 (2007).
Sharma et al., "Receptor tyrosine kinase inhibitors as potent weapons in war against cancers," Curr. Pharm. Des. 15(7):758-776 (2009).
Shaw et al., "Pharmacological Inhibition of Restenosis: Learning From Experience," Trends Pharmacol. Sci. 16(12):401-404 (1995).
Shawver et al., "Receptor Tyrosine Kinases as Targets for Inhibition of Angiogenesis," Drug Discov. Today 2(2):50-63 (1997).
Shayesteh et al., "PIK3CA is implicated as an oncogene in ovarian cancer," Nat. Genet. 21(1):99-102 (1999).
Shimamura and Shapiro, "Heat shock protein 90 inhibition in lung cancer," J. Thorac. Oncol. 3(6 Suppl 2):S152-S159 (2008).
Shimamura et al., "Hsp90 inhibition suppresses mutant EGFR-T790M signaling and overcomes kinase inhibitor resistance," Cancer Res. 68(14):5827-5838 (2008).
Shimamura et al., "on-small-cell lung cancer and Ba/F3 transformed cells harboring the ERBB2 G776insV_G/C mutation are sensitive

(56) References Cited

OTHER PUBLICATIONS to the dual-specific epidermal growth factor receptor and ERBB2 inhibitor HKI-272," Cancer Res. 66(13):6487-6491 (2006).
Sibilia et al., "The epidermal growth factor receptor: from development to tumorigenesis," Differentiation 75(9):770-787 (2007).
Sigal, "Basic science for the clinician 48: tyrosine kinases in disease: the potential for inhibitors in the treatment of immunologic diseases," J. Clin. Rheumatol. 14(1):45-48 (2008).
Simon et al., "By 1023/SK&F 96022: biochemistry of a novel (H+ + K+)-ATPase inhibitor," Biochem Pharmacol. 39(11):1799-1806 (1990).
Singh et al., "Targeted covalent drugs of the kinase family," Curr. Opin. Chem. Biol. 14(4):475-480 (2010) (Epub Jul. 6, 2010).
Singh et al., "The resurgence of covalent drugs," Nat. Rev. Drug Discov. 10(4):307-317 (2011).
Slamon et al., "BCIRG 006: 2nd interim analysis phase III randomized trial comparing doxorubicin and cyclophosphamide followed by docetaxel (AC-T) with doxorubicin and cyclophosphamide followed by docetaxel and trastuzumab (AC-TH) with docetaxel, carboplatin and trastuzumab (TCH) in Her2neu positive early breast cancer patients," In: *San Antonio Breast Cancer Symposium*; 2006 [abstract 52].
Slamon et al., "Human breast cancer: correlation of relapse and survival with amplification of the Her-2/neu oncogene," Science 235(4785):177-182 (1987).
Smith et al. "2006 update of recommendations for the use of white blood cell growth factors: an evidence-based clinical practice guideline,"J. Clin. Oncol. 24(19):3187-3205 (2006) (Epub May 8, 2006).
Smith et al., "2-year follow-up of trastuzumab after adjuvant chemotherapy in HER2-positive breast cancer: a randomised controlled trial." Lancet 369(9555):29-36 (2007).
Smith, "Goals of Treatment of Patients with Metastatic (2006). Breast Cancer," Semin Oncol. 33:S2-S5.
Solca et al., "Beyond Trastuzumab: Second-Generation Targeted Therapies for HER-2-Positive Breast Cancer," Drugs for HER-2-positive Breast Cancer, Milestones in Drug Therapy, 2011 p. 91-107 (2011).
Specht and Gralow, "Neoadjuvant chemotherapy for locally advanced breast cancer," Semin. Radiat. Oncol. 9(4):222-228 (2009).
Spector et al., "Small Molecule HER-2 Tyrosine Kinase Inhibitors," Breast Cancer Res. 9(2):205 (2007).
Spector, "Treatment of metastatic ErbB2-positive breast cancer: options after progression on trastuzumab," Clin. Breast Cancer 8 Suppl 3:S94-S99 (2008).
Spicer and Rudman, "EGFR inhibitors in non-small cell lung cancer (NSCLC): the emerging role of the dual irreversible EGFR/HER2 inhibitor BIBW 2992," Target Oncol. 5(4):245-255 (2010) (Epub Jun. 24, 2010).
Srivastava et al., "Synthesis and structure-activity relationships of potent antitumor active quinoline and naphthyridine derivatives," Anticancer Agents Med. Chem. 7(6):685-709 (2007).
Staroslawska et al. (Dec. 2010). Safety and Efficacy of Neratinib (HKI-272) Plus Vinorelbine in the Treatment of Patients With ErbB2+ Metastatic Breast Cancer Pretreated With Anti-Her2 Therapy. Poster presented at teh 33rd Annual San Antonio Breast Cancer Symposium, San Antonio, Texas.
Stebbing et al., "Lemur tyrosine kinase-3 (LMTK3) in cancer and evolution," Oncotarget 2(6):428-429 (2011).
Steck et al., "Identification of a candidate tumour suppressor gene, MMAC1, at chromosome 10q23.3 that is mutated in multiple advanced cancers," Nat. Genet. 15(4):356-362 (1997).
IEINS et al., "Targeting the epidermal growth factor receptor in non-small cell lung cancer," Onkologie 33(12):704-709 (2010) (Epub Nov. 26, 2010).
Stemke-Hale et al., "An integrative genomic and proteomic analysis of PIK3CA, PTEN, and AKT mutations in breast cancer," Cancer Res. 68(15):6084-6091 (2008).

Stockler et al., "Chemotherapy for advanced breast cancer—how long should it continue?" Breast Cancer Res. Treat. 81(Suppl. 1):549-552 (2003).
Stokoe et al., "Dual role of phosphatidylinositol-3,4,5-trisphosphate in the activation of protein kinase B," Science 277(5325):567-570 (1997).
Sugiyama, "Drug Transporters: Roles in New Drug Discovery and Development," Drug Metab. Rev. 42(S1):1-323 (2010).
Suzuki et al., "Combination of trastuzumab and vinorelbine in metastatic breast cancer," Jpn. J. Clin. Oncol. 33(10):514-517 (2003).
Swaby et al., "Neratinib in combination with trastuzumab for the treatment of advanced breast cancer: A phase I/II study," J. Clin. Oncol. 27:15s(suppl; abstr 1004) (2009).
Tagliabue et al., "HER2 as a target for breast cancer therapy," Expert Opin. Biol. Ther. 10(5):711-724 (2010).
Takada, "API Form Screening and Selection in Drug Discovery Stage," Pharm Stage 6(10):20-25 (2007). [English Translation Not Available].
Tejpar et al., "Phase 1/2a study of EKB-569, an irreversible inhibitor of epidermal growth factor receptor, in combination with 5-fluorouracil, leucovorin, and oxaliplatin (FOLFOX-4) in patients with advanced colorectal cancer (CRC)," J. Clin. Oncol. 22(14S):264s Abstr. 3579 (2004).
Test Procedures and Acceptance Criteria for New Drug Substances and New Drug Products; Pharmaceutical Affairs Bureau Notification No. 568; 2001 [English Translation Not Available].
Therasse et al., "New guidelines to evaluate the response to treatment in solid tumors. European Organization for Research and Treatment of Cancer, National Cancer Institute of the United States, National Cancer Institute of Canada," J. Natl. Cancer Inst. 92(3):205-216 (2000).
Tjin Tham Sjin et al., "Design of a novel covalent EGFR mutant-selective inhibitor," EJC Suppl. 8(7):31 Abstr. 73 (2010).
Toffoli et al., "Pharmacology of epidermal growth factor inhibitors," Int. J. Biol Markers 22(1 Suppl 4):S24-S39 (2007).
Tolaney and Krop, "Mechanisms of trastuzumab resistance in breast cancer," Anticancer Agents Med. Chem. 9(3):348-355 (2009).
Tolaney et al., "HER2-Positive Breast Cancer," JCOM 14(7):395-403 (2007).
Tomillero and Moral, "Gateways to Clinical Trials," Methods Find. Exp. Clin. Pharmacol. 31(3): 183-226 (2009).
Tomillero and Moral, "Gateways to Clinical Trials," Methods Find. Exp. Clin. Pharmacol. 31(10):661-700 (2009).
Tookman and Roylance, "New Drugs for Breast Cancer," Br. Med. Bull. 96:111-129 (2010) (Epub Sep. 23, 2010).
Torres and Harris, "Polycystic kidney disease: genes, proteins, animal models, disease mechanisms and therapeutic opportunities," J. Intern. Med. 261(1):17-31 (2007).
Traxler, "Tyrosine kinase inhibitors in cancer treatment (Part II)," Exp. Opin. Ther. Patents 8(12):1599-1625 (1998).
Tsou et al., "Optimization of 6,7-Disubstituted-4-(Arylamino)Quinoline-3-Carbonitriles as Orally Active, Irreversible Inhibitors of Human Epidermal Growth Factor Receptor-2 Kinase Activity," J. Med. Chem. 48(4):1107-1131 (2005).
Tsou, "American Chemical Society—226th National Meeting. Novel Substituted 4-Anilinoquinoline-3-carbonitriles as orally active, irreversible binding inhibitors of HER-2 Kinase," (abstr. 14) 2003.
Twelves et al., "Erlotinib in combination with capecitabine and docetaxel in patients with metastatic breast cancer: a dose-escalation study," Eur. J. Cancer 44(3):419-426 (2008) (Epub Jan. 30, 2008).
Ullrich et al., "Human epidermal growth factor receptor cDNA sequence and aberrant expression of the amplified gene in A431 epidermoid carcinoma cells," Nature 309(5967):418-425 (1984).
Untch, "Targeted Therapy for Early and Locally Advanced Breast Cancer," Breast Care (Basel) 5(3):144-152 (2010) (Epub Jun. 16, 2010).
Upeslacis, Janis, Meeting at Mcgill University, Canada, Evolution of Kinase Inhibitors at Wyeth, Oct. 16, 2002.
Van Arnum, "Evaluating late-stage pipelines and potential: will 2011 be a more promising year for new molecular entities? A review

(56) References Cited

OTHER PUBLICATIONS of Big Pharma's late-stage pipeline shows what might lie ahead." Pharmaceutical Technology 35.2 (2011): 52+. Expanded Academic ASAP. Web. Jul. 18, 2011.
Van Schaeybroeck et al., "Epidermal growth factor receptor activity determines response of colorectal cancer cells to gefitinib alone and in combination with chemotherapy," Clin. Cancer Res. 11(20):7480-7489 (2005).
Vasudevan et al., "AKT-independent signaling downstream of oncogenic PIK3CA mutations in human cancer," Cancer Cell 16(1):21-32 (2009).
Vazquez et al., "HER2-Positive Breast Cancer: Analysis of Efficacy in Different Groups," Cancer Chemother. Rev. 4(4):224-240 (2009).
Vengerovsky, "Farmacologicheskaya nesovmestimost," Bulleten' sibirskoi medicini 3:49-56 (2003). (English translation of Abstract provided).
Vincent et al., "Anticancer efficacy of the irreversible EGFr tyrosine kinase inhibitor PD 0169414 against human tumor xenografts," Cancer Chemother. Pharmacol. 45(3):231-238 (2000).
Vivanco and Mellinghoff, "Epidermal growth factor receptor inhibitors in oncology," Curr. Opin. Oncol. 22(6):573-578 (2010).
Von Eyben, "Epidermal growth factor receptor inhibition and non-small cell lung cancer," Crit. Rev. Clin. Lab. Sci. 43(4):291-323 (2006).
Vora et al., "Novel Therapeutics in Breast Cancer—Looking to the Future," Update on Cancer Therapeutics 3:189-205 (2009).
Wagner and Kaufmann, "Prospects for the Use of ATR Inhibitors to Treat Cancer," Pharmaceuticals 3:1311-1334 (2010).
Walko and Lindley, "Capecitabine: a review," Clin. Ther. 27(1):23-44 (2005).
Wang et al., "Characterization of HKI-272 covalent binding to human serum albumin," Drug Metab. Dispos. 38(7):1083-1093 (2010) (Epub Apr. 16, 2010).
Ware et al., "A mechanism of resistance to gefitinib mediated by cellular reprogramming and the acquisition of an FGF2-FGFR1 autocrine growth loop," Oncogenesis 2:e39 (2013).
Weber, "Toward a molecular classification of cancer," Toxicology Dec. 5, 2010;278(2):195-198 (2010) (Epub Oct. 24, 2009).
Wen and Drappatz, "Novel therapies for meningiomas," Expert Rev. Neurother. 6(10):1447-1464 (2006).
Wheatley-Price and Shepherd, "Epidermal growth factor receptor inhibitors in the treatment of lung cancer: reality and hopes," Curr. Opin. Oncol. 20(2):162-175 (2008).
Whenham et al., "HER2-positive breast cancer: from trastuzumab to innovatory anti-HER2 strategies," Clin. Breast Cancer 8(1):38-49 (2008).
Widakowich et al., "Molecular targeted therapies in breast cancer: where are we now?" Int. J. Biochem. Cell. Biol. 2007;39(7-8):1375-1387 (2007) (Epub May 4, 2007).
Wissner et al., "Dual irreversible kinase inhibitors: quinazoline-based inhibitors incorporating two independent reactive centers with each targeting different cysteine residues in the kinase domains of EGFR and VEGFR-2," Bioorg. Med. Chem. 15(11):3635-4368 (2007) (Epub Mar. 23, 2007).
Woenckhaus et al., "Prognostic value of PIK3CA and phosphorylated AKT expression in ovarian cancer," Virchows Arch. 450(4):387-395 (2007) (Epub Feb. 15, 2007).
Wondrak, "Redox-directed cancer therapeutics: molecular mechanisms and opportunities," Antioxid. Redox Signal. 11(12):3013-3069 (2009).
Wong et al., "A phase I study with neratinib (HKI-272), an irreversible pan ErbB receptor tyrosine kinase inhibitor, in patients with solid tumors," Clin. Cancer Res. 15(7):2552-2558 (2009) (Epub Mar. 24, 2009).
Wong et al., "HKI-272, an irreversible pan ErbB receptor tyrosine kinase inhibitory: Preliminary phase 1 results in patients with solid tumors," J. Clin. Oncol. 24(18S):125s Abstr. 3018 (2006).
Wong, "Searching for a magic bullet in NSCLC: the role of epidermal growth factor receptor mutations and tyrosine kinase inhibitors," Lung Cancer 60(Suppl 2):S10-S18 (2008).
World Health Organization (2008). *Fact Sheet—Cancer*, No. 297, 2008. Retrieved from http://www.who.int/mediacentre/factsheets/fs297/en/.
World Health Organization (2008). *World Health Statistics*, 2008. Retrieved from http://www.who.int/gho/publications/world_health_statistics/EN_WHS08_Full.pdf?ua=1.
Written Opinion of the International Searching Authority for International Application No. PCT/US2009/047643 dated Dec. 17, 2010.
Wu et al., "Design and synthesis of tetmhydropyridothieno[2,3-d]pyrimidine scaffold based epidermal growth factor receptor (EGFR) kinase inhibitors: the role of side chain chirality and Michael acceptor group for maximal potency," J. Med. Chem. 53(20):7316-7326 (2010).
Wu et al., "Somatic mutation and gain of copy number of PIK3CA in human breast cancer," Breast Cancer Res. 7(5):R609-R616 (2005) (Epub May 31, 2005).
Wu et al., "TAK-285, a Novel HER2/EGFR Inhibitor, Penetrates the CNS in Rats with an Intact Blood Brain Barrier (BBB),"Cancer Res. 69(24 Suppl): Abstr. 5098 (2009).
Wu et al., "Uncommon mutation, but common amplifications, of the PIK3CA gene in thyroid tumors," J. Clin. Endocrinol. Metab. 90(8):4688-4693 (2005) (Epub May 31, 2005).
Wykosky et al., "Therapeutic targeting of epidermal growth factor receptor in human cancer: successes and limitations," Chin. J. Cancer 30(1):5-12 (2011).
Xia et al., "Truncated ErbB2 receptor (p95ErbB2) is regulated by heregulin through heterodimer formation with ErbB3 yet remains sensitive to the dual EGFR/ErbB2 kinase inhibitor GW572016," Oncogene 23(3):646-653 (2004).
Xu et al., "Acquired resistance of lung adenocarcinoma to EGFR-tyrosine kinase inhibitors gefitinib and erlotinib," Cancer Biol. Ther. 9(8):572-582 (2010) (Epub Apr. 26, 2010).
Yamano, "Approach to Crystal Polymorph in Process Research of New Drug," Journal of Synthetic Organic Chemistry, Japan, 65(9):907-913 (2007). [English Translation Not Available].
Yang et al., "MicroRNA expression profiling in human ovarian cancer: miR-214 induces cell survival and cisplatin resistance by targeting PTEN," Cancer Res. 68(2):425-433 (2008).
Yano et al., "HGF-MET in Resistance to EGFR Tyrosine Kinase Inhibitors in Lung Cancer," Curr. Signal Transduct. Ther. 6(2):228-233 (2011).
Yim et al., "Rak functions as a tumor suppressor by regulating PTEN protein stability and function," Cancer Cell 15(4):304-314 (2009).
Yoshida et al., "Targeting epidermal growth factor receptor: central signaling kinase in lung cancer," Biochem. Pharmacol. 80(5):613-623 (2010) (Epub May 24, 2010).
Yoshimura et al., "EKB-569, a new irreversible epidermal growth factor receptor tyrosine kinase inhibitor, with clinical activity in patients with non-small cell lung cancer with acquired resistance to gefitinib," Lung Cancer 51(3):363-368 (2006) (Epub Dec. 20, 2005).
Yuan and Cantley, "PI3K pathway alterations in cancer: variations on a theme," Oncogene 27(41):5497-5510 (2008).
Yun et al., "The T790M mutation in EGFR kinase causes drug resistance by increasing the affinity for ATP," Proc. Natl. Acad. Sci. U.S.A. 105(6):2070-2075 (2008) (Epub Jan. 28, 2008).
Yuza et al., "Allele-dependent variation in the relative cellular potency of distinct EGFR inhibitors," Cancer Biol. Ther. 6(5):661-667 (2007) (Epub Feb. 13, 2007).
Zaczek et al., "The diverse signaling network of EGFR, HER2, HER3 and HER4 tyrosine kinase receptors and the consequences for therapeutic approaches," Histol. Histopathol. 20(3):1005-1015 (2005).
Zagrekova et al., "Drug Treatment of Breast Cancer," Rossijskij Medicinskij Zhurnal 14:605 (2002). (English Translation Not Available).
Zahnow, "ErbB receptors and their ligands in the breast," Expert Rev. Mol. Med. 8(23):1-21 (2006).
Zhang et al. Xenograft Models of Breast Cancer: the Link between Characteristics of Biomarker Expression and the Anti-tumor Effect of the Representative Therapies [abstract]. In: Proceedings of the 101st Annual Meeting of the American Association for Cancer

(56) References Cited

OTHER PUBLICATIONS

Research; Apr. 17-21, 2010; Washington, DC. Philadelphia (PA): AACR; Cancer Res 2010;70(8 Suppl):Abstract nr 647.

Zhang et al., "Advances in preclinical small molecules for the treatment of NSCLC," Expert Opin. Ther. Pat. 19(6):731-751 (2009).

Zhang et al., "Targeting cancer with small molecule kinase inhibitors," Nature 9:28-39 (2009).

Zhao et al., "Nemtinib Reverses ATP-Binding Cassette Bl-Mediaed Chemotherapeutic Drug Resistance in Vitro, in Vivo, and Ex-Vivo," Mol. Pharmacal. 82: 47-58 (2012).

Zhou et al., "Activation of the PTEN/Mtor/STAT3 Pathway in Breast Cancer Stem-Like Cells is Required for Viability and Maintenance," Proc. Natl. Acad. Sci. U.S.A. 104:16158-16163 (2007).

Zhou et al., "EGFR Intron I Polymorphism in Asian Populations and Its Correlation with EGFR Gene Expression and Amplification in Breast Tumor Tissues," Cancer Biol. Ther. 5(11):1445-1449 (2006).

Zhou et al., "Novel Mutant-Selective EGFR Kinase Inhibitors Against EGFR T790M," Nature 462(7276):1070-1074 (2009).

Allen et al., "Potential benefits of the irreversible pan-erbB inhibitor, CI-1033, in the treatment of breast cancer," Senin. Oncol. 29(3 Suppl 11):11-21 (2002).

Avizienyte et al., "Comparison of the EGFR resistance mutation profiles generated by EGFR-targeted tyrosine kinase inhibitors and the impact of drug combinations," Biochem. J. 415(2):197-206 (2008).

Erjala et al., "Concomitant chemoirradiation with vinorelbine and gefitinib induces additive effect in head and neck squamous cell carcinoma cell lines in vitro," Radiother. Oncol. 85(1):138-145 (2007).

Firoozinia et al., "PIK3CA gene amplification and PI3K p110α protein expression in breast carcinoma," Int. J. Med. Sci. 11(6):620-625 (2014).

Gilmer et al., "Impact of common epidermal growth factor receptor and HER2 variants on receptor activity and Inhibition by lapatinib," Cancer Res. 68(2):571-579 (2008).

McNeil et al., "Two targets, one drug for new EGFR inhibitors," J. Natl. Cancer Inst. 98(16):1102-1103 (2006).

Intellectual Property Office of Singapore Examination Report for Singapore Patent Application No. 2013046099 (dated Jan. 21, 2016).

Intellectual Property Office of Singapore Written Opinion for Singapore Patent Application No. 2013046099 (dated Jun. 4, 2015).

State Intellectual Property Office of the People's Republic of China Search Report for Chinese Patent Application No. 201210069340.0 (dated Dec. 11, 2015).

State Intellectual Property Office of the People's Republic of China Office Action for Chinese Patent Application No. 201210069340.0 (dated Dec. 21, 2015).

\* cited by examiner

ANTINEOPLASTIC COMBINATIONS CONTAINING HKI-272 AND VINORELBINE

CROSS REFERENCE TO RELATED APPLICATION

This application is a continuation of U.S. application Ser. No. 13/404,390, filed Feb. 24, 2012, which is a continuation of U.S. application Ser. No. 12/486,153, filed Jun. 17, 2009, which further claims the benefit of U.S. Provisional Application No. 61/073,330, filed Jun. 17, 2008. The foregoing related applications, in their entirety, are incorporated herein by reference.

BACKGROUND OF THE INVENTION

Breast cancer is the most frequently diagnosed malignancy in women and one of the top two causes of cancer-related deaths in women worldwide. The incidence of breast cancer in the world is increasing, and it is estimated that the disease will affect 5 million women in the next decade. Treatments permit control of symptoms, prolongation of survival, and maintenance of quality of life. However, in about 40% to 50% of all patients treated with curative intent, incurable metastatic disease will develop. Since there is no cure for metastatic breast cancer, current therapeutic goals are palliative.

In several cancer types, deregulation of growth factor signaling is observed, associated with a hyperactivation of the ErbB receptors. The ErbB receptor family includes ErbB-1 (also known as HER-1, epidermal growth factor receptor (EGFR)), ErbB-2 (a.k.a. neu or HER-2), HER-3 (a.k.a. ErbB-3), and HER-4 (a.k.a. ErbB-4). Overexpression of ErbB-1 is observed in non-small cell lung cancer (NSCLC) (40%-80%), breast cancer (14%-91%), and pancreatic cancer (30%-89%). In NSCLC, activation by mutation of amplification of ErbB-1 also occurs in 10% to 30% of patients.

Overexpression of ErbB-2, usually resulting from erbB-2 gene amplification, is observed in tumor tissue in 25% to 30% of patients of patients with metastatic breast cancer (MBC) and is associated with malignant transformation. ErbB-2 overexpression is usually associated with a more aggressive tumor phenotype, worse overall prognosis, and faster relapse times at all stages of cancer development. In women with MBC, this overexpression confers a relative resistance to treatment with either anthracycline/alkylator- or taxane-based chemotherapy. ErbB-2 overexpression in tumorigenesis has been mainly studied in breast cancers but is also observed in other cancers.

Among current therapeutics for cancers, specifically those characterized by overexpression of ErbB-2, are vinorelbine, trastuzumab and HKI-272. Vinorelbine, a semisynthetic vinca alkaloid having broad antitumor activity, acts through microtubule disruption. Vinorelbine presents a lower neurotoxicity profile than vincristine or vinblastine. Vinorelbine has been shown to be less toxic to axonal microtubules than vincristine or vinblastine at therapeutic concentrations. In studies conducted on subjects with advanced breast cancer, treatment with vinorelbine as a single agent is at least as efficient as other chemotherapies but with a lower risk of toxicity. However, the risk of toxicity increases in parallel with the number of previous anticancer treatments.

Trastuzumab (HERCEPTIN® drug) is a humanized monoclonal antibody specific for the extracellular domain of ErbB-2. It presents significant clinical benefit and significant antitumor activity when used alone or in combination with taxanes in metastatic breast cancer in first-line treatment or in patients who have tumor progression after chemotherapy. Because of the improvement in survival, trastuzumab-based therapies have become standard of care for women with ErbB-2-positive MBC. For women with advanced or metastatic disease, breast cancer eventually recurs despite trastuzumab treatment. Trastuzumab-based therapy is also associated with potential cardiac toxicity. Certain breast cancer cells are resistant to trastuzumab due to the occurrence of secondary ErbB-2 mutations, such as truncation of extracellular domain ErbB-2 receptor. Such mutations can result in cancer cells which are not recognized by the antibody.

In recent studies, trastuzumab in combination with either vinorelbine or taxane (paclitaxel with or without carboplatin, or docetaxel) was utilized to treat subjects with ErbB-2-overexpressing MBC. As expected, the most frequent grade toxicity observed with the combination of trastuzumab and vinorelbine was neutropenia.

HKI-272 is a small molecule, irreversible pan-ErbB receptor inhibitor specific for epidermal growth factor receptor (ErbB-1 or EGFR), ErbB-2 (HER-2), and ErbB-4 (HER-4). HKI-272 blocks kinase activity of the receptor through binding to the intracellular adenosine triphosphate (ATP) binding site of the receptor. HKI-272 blocks ErbB receptor autophosphorylation in cells at doses consistent with inhibition of cell proliferation. In vitro, HKI-272 alone inhibits kinase activity of ErbB-1, ErbB-2, and HER-4, inhibits tumor cell growth with breast and lung tumor cell lines, and presents a potent growth inhibition of lung cancer cells resistant to gefitinib or erlotinib. In vivo, HKI-272 blocks tumor growth in xenograft animal models. Overall, HKI-272 is less potent against ErbB-1-dependent tumors than ErbB-2-dependent tumors in vivo, even though it has equivalent activity against the 2 kinases in vitro.

There remains a need in the art for therapeutic methods, regimens, compositions, and kits which are useful in treating metastatic breast cancer and solid tumors.

SUMMARY OF THE INVENTION

This invention addresses the need in the art by providing regimens, compositions and methods using a HKI-272 compound and a vinorelbine compound for the treatment of cancers, such as solid tumors and metastatic breast cancer.

In one aspect, regimens for treating a neoplasm in a subject are provided and include administering a vinorelbine compound and administering a HKI-272 compound. Desirably, the vinorelbine compound is vinorelbine and the HKI-272 compound is HKI-272. In one embodiment, the neoplasm is breast cancer.

In another aspect, a regimen for treating a solid tumor associated with overexpression or amplification of HER-2 in a subject is provided, wherein one cycle of the regimen includes 21 days. The regimen includes orally administering at least one unit dose of HKI-272 starting on day 1 of the cycle and intravenously administering at least one unit dose of vinorelbine on days 1 and 8 of the cycle.

In a further aspect, a regimen for treating a metastatic cancer associated with overexpression or amplification of HER-2 in a subject is provided. One cycle of the regimen includes 21 days and the regimen includes orally administering at least one unit dose of HKI-272 starting on day 2 of the cycle and intravenously administering at least one unit dose of vinorelbine on days 1 and 8 of the cycle.

In still another aspect, a product comprising a vinorelbine compound and HKI-272 compound is provided as a combined preparation for simultaneous, separate or sequential use in treating a neoplasm in a mammal.

In yet a further aspect, a pharmaceutical pack for treating a neoplasm in one individual mammal is provided and includes (a) at least one unit dose of vinorelbine; and (b) at least one unit dose of HKI-272.

In another aspect, a pharmaceutical composition is described and contains vinorelbine, HKI-272, and at least one pharmaceutically acceptable carrier.

In still another aspect, a method of treating a neoplasm associated with overexpression or amplification of HER-2 in a mammal in need thereof is provided and includes administering a unit dose of a vinorelbine compound and administering a unit dose of a HKI-272 compound.

Other aspects and advantages of the invention will be readily apparent from the following detailed description of the invention.

DESCRIPTION OF THE INVENTION

This invention provides compositions, methods, and regimens using a combination of a HKI-272 compound and a vinorelbine compound for the treatment of cancers. This invention provides in one embodiment compositions comprising HKI-272 and vinorelbine for the treatment of neoplasms. Also provided are products containing HKI-272 and vinorelbine formulated for simultaneous, separate or sequential use in treating neoplasms in a mammal. The invention is also useful as an adjuvant and/or neoadjuvant therapy of earlier stages of breast cancer. The invention provides, in another embodiment, methods for the combined use or administration of a HKI-272 compound and vinorelbine compound.

The Therapeutic Regimen and its Components

Without wishing to be bound by theory, the inventors hypothesize that the combination of HKI-272 and vinorelbine for treating a neoplasm is desirable because HKI-272 targets the intracellular ErbB-2 kinase rather than the extracellular domain. Thus, this combination has different mechanisms of sensitivity and resistance, and then presents an advantage over the therapeutic combination of trastuzumab and vinorelbine. Further, the combination of HKI-272 and vinorelbine is anticipated to be more effective than combinations of vinorelbine with other pan-ErbB inhibitors due to the tyrosine kinase inhibition activity of HKI-272 through an irreversible binding at a targeted cysteine residue in the ATP binding pocket of the receptor.

These methods, combinations and products are useful in the treatment of a variety of neoplasms, particularly those associated with overexpression or amplification of HER-2. In one embodiment, the neoplasm is a solid tumor or an advanced solid tumor. In a further embodiment, the neoplasm is metastatic. In another embodiment, neoplasms that may be treated as described herein include, e.g., lung cancers (such as bronchioalveolar carcinoma and non small cell lung cancer), breast cancers (such as metastatic breast cancer and HER-2-positive breast cancer), prostate cancers, myeloma, head and neck cancer, transitional cell carcinoma, small cell and large cell neuroendocrine carcinoma of the uterine cervix. In still another embodiment, the neoplasm is resistant to trastuzumab.

The regimens, methods, and compositions described herein include the concurrent, simultaneous, sequential or separate administration of the components, i.e., a HKI-272 compound and a vinorelbine compound. The term "composition" as used herein is intended to cover both pharmaceutical compositions in which 2 or more components are mixed, compositions of matter such as pharmaceutical kits and packs in which the components are individually packaged for concurrent, simultaneous, sequential, or separate administration. In one aspect of the invention, "a combination" includes simultaneous administration of the HKI-272 and vinorelbine compounds. In a further aspect of the invention, "a combination" includes sequential administration of the HKI-272 and vinorelbine compounds. In one embodiment the HKI-272 is administered before the vinorelbine compound. In another embodiment the vinorelbine compound is administered before the HKI-272 compound. In another aspect, "a combination" includes separate administration of the HKI-272 and vinorelbine compounds in a particular therapeutic regimen in which the two components of the combination are administered at specific times and amounts with respect to each other. In one embodiment, the combination of the HKI-272 and vinorelbine compounds produces a more beneficial therapeutic effect than that achievable by the administration of either a HKI-272 compound alone or a vinorelbine compound alone. Where the administration of those agents is sequential or separate, the delay in administering the second component should not be such as to lose the benefits provided the combination therapy.

In one embodiment, the combination of the HKI-272 and vinorelbine compounds is particularly well suited for treatment of metastatic breast cancer. In another embodiment, the combination of the HKI-272 and vinorelbine compounds are well suited for treatment of breast, kidney, bladder, mouth, larynx, esophagus, stomach, colon, ovary, and lung), and polycystic kidney disease.

As used herein and except where noted, the terms "individual", "subject" and "patient" are used interchangeably, and refer to any animal, including mammals, preferably mice, rats, other rodents, rabbits, dogs, cats, swine, cattle, sheep, horses, non-human primates, and humans. Desirably, the term "individual", "subject" or "patient" refers to a human. In certain circumstances, these terms refer to experimental animals such as rabbits, rats, and mice, and other animals. In most embodiments, the subjects or patients are in need of the therapeutic treatment. Accordingly, the term "subject" or "patient" as used herein means any mammalian patient or subject to which the HKI-272 and vinorelbine compounds can be administered. In one embodiment, to identify subject patients for treatment according to the methods of the invention, accepted screening methods are employed to determine risk factors associated with a targeted or suspected disease or condition or to determine the status of an existing disease or condition in a subject. These screening methods include, e.g., conventional work-ups to determine risk factors that are associated with the targeted or suspected disease or condition. These and other routine methods allow the clinician to select patients in need of therapy using the methods and formulations of the present invention. In one embodiment, the "individual", "subject" or "patient" may have had no previously chemotherapeutic treatment. In another embodiment, the "individual", "subject" or "patient" may have previously undergone chemotherapeutic treatment. In another embodiment, the "individual", "subject" or "patient" may have previously been administered an aniloquinazoline class inhibitor. In a further embodiment, the "individual", "subject" or "patient" may have previously been administered lapatinib or geftinib as the aniloquinazoline class inhibitor. Desirably, the blood count of the patient prior to treatment with the described combinations is stable enough to permit administration of the combinations described herein. In one embodiment, the neutrophil count of the patient prior to administration of the vinorelbine and HKI-272 compounds is at least 1500. In another embodiment, the platelet count of the patient prior to administration of the vinorelbine and HKI-272 compounds is at least 100,000/L.

As used herein, "a HKI-272 compound" refers, in one embodiment, to a compound having the following core structure:

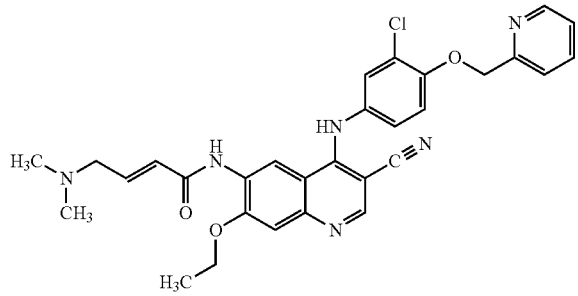 [SMILES: CCOc1cc2ncc(C#N)c(Nc3ccc(OCc4ccccn4)c(Cl)c3)c2cc1NC(=O)/C=C/CN(C)C]

or a derivative or pharmaceutically acceptable salt thereof. Suitable derivatives may include, e.g., an ester, ether, or carbamate. The core structure represented above is a particularly HKI-272 compound, called HKI-272, which has the chemical name (E)-N-{4-[3-chloro-4-(2-pyridinylmethoxy)anilino]-3-cyano-7-ethoxy-6-quinolinyl}-4-(dimethylamino)-2-butenamide. In one embodiment, the HKI-272 compound useful in the compositions and methods described herein is HKI-272.

In another embodiment, an HKI-272 compound has the structure:

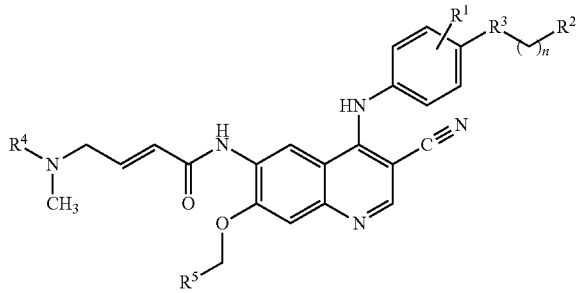

wherein:
$R^1$ is halogen;
$R^2$ is pyridinyl, thiophenyl, pyrimidinyl, thiazolyl, or phenyl, wherein $R^2$ is optionally substituted with up to three substituents;
$R^3$ is O or S;
$R^4$ is $CH_3$ or $CH_2CH_2OCH_3$;
$R^5$ is $CH_3$ or $CH_2CH_3$; and
n is 0 or 1.

The term "halogen" as used herein refers to Cl, Br, I, and F.

These HKI-272 compounds, of which HKI-272 is a species, are characterized by the ability to act as potent HER-2 inhibitors. See, e.g., U.S. Pat. Nos. 6,288,082 and 6,297,258 and US Patent Application Publication No. 2007/0104721, which are hereby incorporated by reference. These compounds and their preparation are described in detail in US Patent Application Publication No. 2005/0059678, which is hereby incorporated by reference. For convenience, "a HKI-272 compound" is used throughout this specification. However, any compound of the structure(s) provided above can be substituted for HKI-272 in the combinations described in detail below.

HKI-272, other HKI-272 compounds, and methods of making and formulating same have been described. See, e.g., US Patent Application Publication No. 2005/0059678 and U.S. Pat. No. 6,002,008, which are hereby incorporated by reference. The methods described in these documents can also be used to prepare the substituted 3-quinoline compounds used herein and are hereby incorporated by reference. In addition to the methods described in these documents, International Patent Publication Nos. WO-96/33978 and WO-96/33980, which are hereby incorporated by reference, describe methods that are useful for the preparation of these HKI-272 compounds. Although these methods describe the preparation of certain quinazolines, they are also applicable to the preparation of correspondingly substituted 3-cyanoquinolines and are hereby incorporated by reference.

As used herein, the term "a vinorelbine compound" means vinorelbine or a pharmaceutically acceptable salt thereof, which has broad antitumor activity and that acts through microtubule disruption. See, Widakowich et al., Anticancer Agents Med. Chem., 8(5):488-496 (June 2008) and Wissner et al., Arch. Pharm. (Weinheim), (May 20, 2008 e-publication). The term includes the neutral vinorelbine compound, i.e., 4-(acetyloxy)-6,7-didehydro-15-((2R,6R,8S)-4-ethyl-1,3,6,7,8,9-hexohydro-8-(methoxycarbonyl)-2,6-methano-2H-azecino(4,3-b)indol-8-yl)-3-hydroxy-16-methoxy-1-methyl, methyl ester, (2β, 3β, 4β, 5α, 12R, 19α)-aspidospermidine-3-carboxylic acid (vinorelbine; tradename: Navelbine). Vinorelbine and its pharmaceutically acceptable salts are available from commercial vendors including Adventrx/SD Pharmaceuticals (SDP-012® drug), Hana (ALOCREST® drug), and Inex Pharmaceuticals Corp. (INX-0125™ drug), and other vinorelbine compounds, including those discussed in U.S. Pat. No. 7,235,564, which is hereby incorporated by reference. In one embodiment, a vinorelbine compound includes a compound with a structural similarity to the vinorelbine compound structure below, e.g., compounds with a similar alkaloid structure that have been modified to enhance therapeutic benefit.

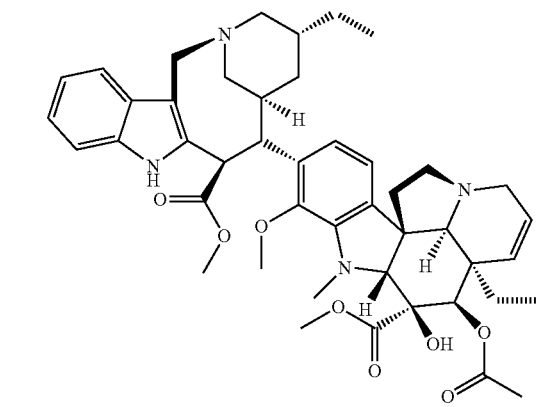

The preparation of vinorelbine compounds are described by Langlois et al., in J. Am. Chem. Soc. 98:7017-7024 (1976); and by Mangeney et al., in Tetrahedron, 35:2175-2179 (1979).

The HKI-272 and vinorelbine compounds and corresponding pharmaceutically acceptable salts or esters thereof include isomers either individually or as a mixture, such as enantiomers, diastereomers, and positional isomers.

"Pharmaceutically acceptable salts and esters" refers to salts and esters that are pharmaceutically acceptable and have the desired pharmacological properties. Such salts include, e.g., salts that can be formed where acidic protons present in the compounds are capable of reacting with inorganic or organic bases. Suitable inorganic salts include, e.g., those formed with the alkali metals or alkaline earth metals, e.g. sodium and potassium, magnesium, calcium, and aluminum. Suitable organic salts include, e.g., those formed with organic bases such as the amine bases, e.g. ethanolamine, diethanolamine, triethanolamine, tromethamine, N-methylglucamine, and the like. Pharmaceutically acceptable salts can also include acid addition salts formed from the reaction of basic moieties, such as amines, in the parent compound with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid).

Pharmaceutically acceptable esters include esters formed from carboxy, sulfonyloxy, and phosphonoxy groups present in the compounds of the invention, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds utilized herein may be present in unsalified or unesterified form, or in salified and/or esterified form, and the naming of such compounds is intended to include both the original (unsalified and unesterified) compound and its pharmaceutically acceptable salts and esters. Also, one or more compounds utilized herein may be present in more than one stereoisomeric form, and the naming of such compounds is intended to include all single stereoisomers and all mixtures (whether racemic or otherwise) of such stereoisomers.

Pharmaceutically acceptable salts of the HKI-272 and vinorelbine compounds with an acidic moiety may be formed from organic and inorganic bases including, e.g., salts with alkali metals or alkaline earth metals such as sodium, potassium, lithium, calcium, or magnesium or organic bases and N-tetraalkylammonium salts such as N-tetrabutylammonium salts.

Similarly, when one or more compound utilized herein contains a basic moiety, salts may be formed from organic and inorganic acids. For example, salts may be formed from acids such as acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids when a compound of this invention contains a basic functional group. Other suitable examples of pharmaceutically acceptable salts include, but are not limited, to sulfate; citrate, acetate; oxalate; chloride; bromide; iodide; nitrate; bisulfate; phosphate; acid phosphate; isonicotinate; lactate; salicylate; acid citrate; tartrate; oleate; tannate; pantothenate; bitartrate; ascorbate; succinate; maleate; gentisinate; fumarate; gluconate; glucaronate; saccharate; formate; benzoate; glutamate; methanesulfonate; ethanesulfonate; benzenesulfonate; p-toluenesulfonate; pamoate (i.e., 1,1'-methylene-bis-(2-hydroxy-3-naphthoate)); and salts of fatty acids such as caproate, laurate, myristate, palmitate, stearate, oleate, linoleate, and linolenate salts. In one embodiment, the vinorelbine compound is vinorelbine tartrate.

The compounds can also be used in the form of esters, carbamates and other conventional ester forms, also referred to herein as prodrug forms, which when administered in such form, convert to the active moiety in-vivo. Exemplary ester forms of the compounds of this invention include, but are not limited to, straight chain alkyl esters having from 1 to 6 carbon atoms or branched chain alkyl groups containing 1 to 6 carbon atoms, including methyl, ethyl, propyl, butyl, 2-methylpropyl and 1,1-dimethylethyl esters, cycloalkyl esters, alkylaryl esters, benzyl esters, and the like.

Accordingly, a pharmaceutical composition is provided and contains effective amounts of the HKI-272 and vinorelbine compounds in combination or association with one or more pharmaceutically acceptable carrier. Suitable examples of pharmaceutical carriers used herein include, but are not limited to, excipients, diluents, fillers, disintegrants, lubricants and other agents that can function as a carrier. The term "pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. Pharmaceutical compositions are prepared in accordance with acceptable pharmaceutical procedures, such as described in Remingtons Pharmaceutical Sciences, 17th edition, ed. Alfonoso R. Gennaro, Mack Publishing Company, Easton, Pa. (1985). Pharmaceutically acceptable carriers are those that are compatible with the other ingredients in the formulation and biologically acceptable. Suitable pharmaceutically-acceptable excipients or carriers for a tablet or caplet formulation include, e.g., inert excipients such as lactose, sodium carbonate, calcium phosphate or calcium carbonate, granulating and disintegrating agents such as corn starch or alginic acid; binding agents such as gelatin or starch; lubricating agents such as magnesium stearate, stearic acid or talc; preservative agents such as ethyl or propyl 4-hydroxybenzoate, and anti-oxidants, such as ascorbic acid. Tablet or caplet formulations may be uncoated or coated either to modify their disintegration and the subsequent absorption of the active ingredient within the gastrointestinal tract, or to improve their stability and/or appearance using conventional coating agents and procedures well known in the art. In one embodiment, the weight of the tablet is at least about 20, 30, 40, 50, 60, or 70 mg.

Optional Components of the Regimens

The regimens described herein may also include the administration of other agents. In one embodiment, the regimen further includes administration of a taxane, e.g., docetaxel and paclitaxel [e.g., a suspension of paclitaxel bound to albumen nanoparticles, which is available as the ABRAXANE® reagent]. Paclitaxel may also be administered on a weekly schedule at doses 60-100 mg/m² administered over 1 hour, weekly, or 2-3 weekly doses followed by a one week rest. In one embodiment, paclitaxel is administered intravenously over 3 hours at a dose of 175 mg/m², optionally followed by cisplatin at a dose of 75 mg/m²; or paclitaxel administered intravenously over 24 hours at a dose of 135 mg/m², optionally followed by cisplatin at a dose of 75 mg/m². In patients previously treated with therapy for carcinoma, paclitaxel can be injected at several doses and schedules. However, the optimal regimen is not yet clear. The recommended regimen is paclitaxel 135 mg/m² or 175 mg/m² administered intravenously over 3 hours every 3 weeks. These doses may be altered as needed or desired.

In another embodiment, other active agents may be included in a combination with an HKI-272 compound and vinorelbine compound and include, e.g., chemotherapeutic agents, such as alkylating agents or mTOR inhibitors (rapamycin and derivatives thereof); hormonal agents (i.e., estramustine, tamoxifen, toremifene, anastrozole, or letrozole); antibiotics (i.e., plicamycin, bleomycin, mitoxantrone, idarubicin, dactinomycin, mitomycin, or daunorubicin); other antimitotic agents (i.e., vinblastine, vincristine, teniposide); topoisomerase inhibitors (i.e., topotecan, irinotecan, etoposide, or doxorubicin, e.g., CAELYX™ or DOXIL® reagents, pegylated liposomal doxorubicin hydrochloride); and other agents (i.e., hydroxyurea, altretamine, rituximab, paclitaxel, docetaxel, L-asparaginase, or gemtuzumab ozogamicin); biochemical modulating agents, imatib, EGFR inhibitors such as EKB-569 or other multi-kinase inhibitors, e.g., those that targets serine/threonine and receptor tyrosine kinases in both the tumor cell and tumor vasculature, or immunomodulators (i.e., interferons, IL-2, or BCG). Examples of suitable interferons include interferon α, interferon β, interferon γ, and mixtures thereof.

Desirably, the combination of the HKI-272 compound and vinorelbine compound may be further combined with antineoplastic alkylating agents, e.g., those described in US Patent Application Publication No. 2002-0198137, which is hereby incorporated by reference. Antineoplastic alkylating agents are roughly classified, according to their structure or reactive moiety, into several categories which include nitrogen mustards, such as MUSTARGEN® drug (meclorethamine), cyclophosphamide, ifosfamide, melphalan, and chlorambucil; azidines and epoxides, such as thiotepa, mitomycin C, dianhydrogalactitol, and dibromodulcitol; alkyl sulfinates, such as busulfan; nitrosoureas, such as bischloroethylnitrosourea (BCNU), cyclohexyl-chloroethylnitrosourea (CCNU), and methylcyclohexylchloroethylnitrosourea (MeCCNU); hydrazine and triazine derivatives, such as procarbazine, dacarbazine, and temozolomide; streptazoin, melphalan, chlorambucil, carmustine, methclorethamine, lomustine) and platinum compounds. Platinum compounds are platinum containing agents that react preferentially at the N7 position of guanine and adenine residues to form a variety of monofunctional and bifunctional adducts. (Johnson S W, Stevenson J P, O'Dwyer P J. Cisplatin and Its Analogues. In Cancer Principles & Practice of Oncology 6$^{th}$ Edition. ed. DeVita V T, Hellman S, Rosenberg S A. Lippincott Williams & Wilkins. Philadelphia 2001. p. 378.) These compounds include cisplatin, carboplatin, platinum IV compounds, and multinuclear platinum complexes. Representative examples of alkylating agents including meclorethamine (injectable; MUSTARGEN® drug), cyclophosphamide (injectable; cyclophosphamide, lyophilized CYTOXAN® drug, or NEOSAR® drug; oral tablets cyclophosphamide or CYTOXAN® drug), ifosfamide (injectable; IFEX), melphalan (injectable, ALKERAN® drug; and oral tablets, ALKERAN® drug), chlorambucil (oral tablets, LEUKERAN® drug), thiotepa (injectable, thiotepa or THIOPLEX® drug), mitomycin (injectable, mitomycin or MUTAMYCIN® drug), busulfan (injectable, BUSULFEX® drug; oral tablets, MYLERAN® drug), lomustine (oral capsules; CEENU), carmustine (intracranial implant, GLIADEL); injectable (BICNU), procarbazine (oral capsules, MATULANE® drug), temozolomide (oral capsules, TEMODAR® drug), cisplatin (injectable, cisplatin, PLATINOL® drug, or PLATINOL®-AQ), carboplatin (injectable, PARAPLATIN® drug), and oxaliplatin (ELOXATIN® drug).

In another embodiment, a combination described herein may further include an antineoplastic antimetabolite, as described in US Patent Application Publication Nos. 2005/0187184 or 2002/0183239, which are hereby incorporated by reference. As used herein accordance, the term "antimetabolite" means a substance which is structurally similar to a critical natural intermediate (metabolite) in a biochemical pathway leading to DNA or RNA synthesis which is used by the host in that pathway, but acts to inhibit the completion of that pathway (i.e., synthesis of DNA or RNA). More specifically, antimetabolites typically function by (1) competing with metabolites for the catalytic or regulatory site of a key enzyme in DNA or RNA synthesis, or (2) substitute for a metabolite that is normally incorporated into DNA or RNA, and thereby producing a DNA or RNA that cannot support replication. Major categories of antimetabolites include (1) folic acid analogs, which are inhibitors of dihydrofolate reductase (DHFR); (2) purine analogs, which mimic the natural purines (adenine or guanine) but are structurally different so they competitively or irreversibly inhibit nuclear processing of DNA or RNA; and (3) pyrimidine analogs, which mimic the natural pyrimidines (cytosine, thymidine, and uracil), but are structurally different so thy competitively or irreversibly inhibit nuclear processing of DNA or RNA. Representative examples of antimetabolites include, without limitation, 5-Fluorouracil (5-FU; 5-fluoro-2,4(1H,3H)-pyrimidinedione; topical cream, FLUOROPLEX® or EFUDEX® drugs; topical solution, FLUOROPLEX® or EFUDEX® drugs; injectable, ADRUCIL® drug or flurouracil), floxuradine (2'-deoxy-5-fluorouridine; injectable, FUDR or floxuradine), thioguanine (2-amino-1,7-dihydro-6-H-purine-6-thione (oral tablets, thioguanine), cytarabine (4-amino-1-((3)-D-arabinofuranosyl-2(1H)-pyrimidinone; liposomal injectable, DEPOCYT® reagent; liquid injectable, cytarabine or CYTOSAR-U® drug), fludarabine (9-H-Purin-6-amine,2-fluoro-9-(5-O-phosphono-(β)-D-a-rabinofuranosyl; liquid injectable, FLUDARA), 6-Mercaptopurine (1,7-dihydro-6H-purine-6-thione; oral tablets, PURINETHOL), methotrexate (MTX; N-[4-[[(2,4-diamino-6-pteridinyl)methyl]methylamino]benzoyl]-L-glutamic acid; liquid injectable, methotrexate sodium or FOLEX; oral tablets, methotrexate sodium), gemcitabine (2'-deoxy-2',2'-difluorocytidine monohydrochloride ((β)-isomer); liquid injectable, GEMZAR), capecitabine (5'-deoxy-5-fluoro-N-[(pentyloxy)carbonyl]-cytidine; oral tablet, XELODA), pentostatin ((R)-3-(2-deoxy-(beta)-D-erythro-pentofuranosyl)-3,6,7,8-tetrahydroimidazo[4,5-d][1,3]diazepin-8-ol; liquid injectable, NIPENT), trimetrexate (2,4-diamino-5-methyl-6-[(3,4,5-trimethoxyanilino) methyl]quinazoline mono-D-glucuronate; liquid injectable, NEUTREXIN), cladribine (2-chloro-6-amino-9-(2-deoxy-(β)-D-erythropento-furanosyl) purine; liquid injectable, LEUSTATIN).

The term "biochemical modulating agent" is well known and understood to those skilled in the art as an agent given as an adjunct to anti-cancer therapy, which serves to potentate its antineoplastic activity, as well as counteract the side effects of the active agent, e.g., an antimetabolite. Leucovorin and levofolinate are typically used as biochemical modulating agents for methotrexate and 5-FU therapy. Leucovorin (5-formyl-5,6,7,8-tetrahydrofolic acid) is commercially available as an injectable liquid (leucovorin calcium or WELLCOVORIN) and as oral tablets (leucovorin calcium). Levofolinate (pharmacologically active isomer of 5-formyltetrahydrofolic acid) is commercially available as an injectable containing (ISOVORIN) or as oral tablets (ISOVORIN).

In still another embodiment, the combination further includes a kinase inhibitor. Particularly desirable kinase inhibitors include multi-kinase inhibitors target serine/threonine and receptor tyrosine kinases in both the tumor cell and tumor vasculature. Examples of suitable kinase inhibitors include, without limitation, sorafenib (BAY 43-9006, commercially available as NEXAVAR), which has been granted Fast Track status by the FDA for metastatic renal cell cancer, zarnestra (R115777, tipifarnib), suntinib (SUTENT), and other compounds that target Ras/Raf/MEK and/or MAP kinases including, e.g., avastin, ISIS 5132, and MEK inhibitors such as CI-1040 or PD 0325901. Alternatively, the kinase inhibitor may be administered to the patient prior to or subsequent to treatment with the vinorelbine compound and/or HKI-272 compound.

In still further embodiment, the combination may include an anti diarrheal. One of skill in the art would readily be able to select a suitable antidiarrheal for use herein including, without limitation, loperamide or diphenoxylate hydrochloride and atropine sulfate. Alternatively, the anti-diarrheal may be administered to the patient prior to or subsequent to treatment with the vinorelbine compound and/or HKI-272 compound.

In a further embodiment, the combination further contains an antiemetic agent. Examples of antiemetic agents include, without limitation, metoclopramide, Dolasetron, Granisetron, Ondansetron, Tropisetron, and Palonosetron, among others. Alternatively, the antiemetic may be administered to the patient prior to or subsequent to treatment with the vinorelbine compound and/or HKI-272 compound.

In yet a further embodiment, the combination also contains an antihistamine. Examples of antihistamines include, without limitation, Cyclizine, Diphenhydramine, Dimenhydrinate (Gravol), Meclizine, Promethazine (Pentazine, Phenergan, Promacot), or Hydroxyzine, among others. Alternatively, the antihistamine may be administered to the patient prior to or subsequent to treatment with the vinorelbine compound and/or HKI-272 compound.

In yet another embodiment, the combination may include a growth factor to prevent and/or treat neutropenia. Such growth factors may readily be selected by those skill in the art according to practice guidelines from the American Society of Clinical Oncology (ASCO; 2006). Alternatively, the growth factor may be administered to the patient prior to or subsequent to treatment with the vinorelbine compound and/or HKI-272 compound.

Administration of the Compositions/Combinations

As used herein, the term "effective amount" or "pharmaceutically effective amount" refers to the amount of active compound or pharmaceutical agent that elicits the biological or medicinal response in a tissue, system, animal, individual or human that is being sought by a researcher, veterinarian, medical doctor or other clinician, which includes one or more of the following; (1) preventing the disease; e.g., preventing a disease, condition or disorder in an individual that may be predisposed to the disease, condition or disorder but does not yet experience or display the pathology or symptomatology of the disease; (2) inhibiting the disease; e.g., inhibiting a disease, condition or disorder in an individual that is experiencing or displaying the pathology or symptomatology of the disease, condition or disorder (i.e., arresting or slowing further development of the pathology and/or symptomatology); and (3) ameliorating the disease; e.g., ameliorating a disease, condition or disorder in an individual that is experiencing or displaying the pathology or symptomatology of the disease, condition or disorder (i.e., reversing the pathology and/or symptomatology). For example, an effective amount," when administered to a subject to treat cancer, is sufficient to inhibit, slow, reduce, or eliminate tumor growth in a subject having cancer.

Use of a combination of the HKI-272 compound and vinorelbine compound also provides for the use of combinations of each of the agents in which one or both agent is used at subtherapeutically effective dosages. Subtherapeutically effective dosages may be readily determined by one of skill in the art, in view of the teachings herein. In one embodiment, the subtherapeutically effective dosage is a dosage which is effective at a lower dosage when used in the combination regimen described herein, as compared to the dosage that is effective when used alone. Also provided are one or more of the active agents in the combinations herein to be used in a supratherapeutic amount, i.e., at a higher dosage in the combination than when used alone. In this embodiment, the other active agent(s) may be used in a therapeutic or subtherapeutic amount.

The term "treating" or "treatment" refers to any indicia of success in amelioration of an injury, pathology, or condition, including any objective or subjective parameter such as abatement; remission; diminishing of symptoms or making the injury, pathology, or condition more tolerable to the patient; slowing the rate of degeneration or decline; making the final point of degeneration less debilitating; or improving a subject's physical or mental well-being. The treatment or amelioration of symptoms can be based on objective or subjective parameters; including the results of a physical examination, neurological examination, and/or psychiatric evaluation. Accordingly, the term "treating" includes the administration of the HKI-272 and vinorelbine compounds to a subject to prevent or delay, to alleviate, or to arrest or inhibit development of the symptoms or conditions associated with cancers, including tumor growth associated with cancer. A skilled medical practitioner will know how to use standard methods to determine whether a patient is suffering from a disease associated with cancer by examining the patient and determining whether the patient is suffering from cancer.

As used herein, the term "providing" with respect to providing a HKI-272 compound and a vinorelbine compound, means either directly administering the HKI-272 compound and vinorelbine compound, or administering a prodrug, derivative, or analog which will form an effective amount of the HKI-272 compound and/or vinorelbine compound within the body.

The invention therefore includes administering an HKI-272 compound and vinorelbine compound to a patient for the treatment of a neoplasm in a patient. In one embodiment, the HKI-272 compound is administered separately from the vinorelbine compound. In a further embodiment, the HKI-272 compound is administered prior to the vinorelbine compound. In another embodiment, the HKI-272 compound is administered subsequent to the vinorelbine compound. In still another embodiment, the HKI-272 compound and the vinorelbine compound are administered simultaneously, but separately. In one embodiment, the HKI-272 compound and the vinorelbine compound are administered together as a combined preparation.

In one embodiment, a product contains an HKI-272 compound and vinorelbine compound as a combined preparation for simultaneous, separate or sequential use in treating a neoplasm in a mammal in need thereof. In one embodiment, the HKI-272 compound is separately formulated from the vinorelbine compound. In another embodiment, a product contains the HKI-272 compound and the vinorelbine compound as a combined preparation for simultaneous, separate or sequential use in a neoplasm in a mammal in need thereof.

In one embodiment, a pharmaceutical pack contains a course of treatment of a neoplasm for one individual mammal, wherein the pack contains units of an HKI-272 compound in unit dosage form and units of a vinorelbine compound in unit dosage form. In another embodiment, a pharmaceutical pack contains a course of treatment of a neoplasm for one individual mammal, wherein the pack contains units of an HKI-272 compound in unit dosage form and units of a vinorelbine compound in unit dosage form. In yet another embodiment, a pharmaceutical pack as described herein contains a course of treatment of metastatic breast cancer for one individual mammal.

Administration of the individual components or a composition containing two or more of the individual components may employ any suitable route. Such routes may be selected from, e.g., oral, intravenous (i.v.), respiratory (e.g., nasal or intrabronchial), infusion, parenteral (aside from i.v., such as intralesional, intraperitoneal and subcutaneous injections), intraperitoneal, transdermal (including all administration across the surface of the body and the inner linings of bodily passages including epithelial and mucosal tissues), and vaginal (including intrauterine administration). Other routes of administration are also feasible and include, without limitation, liposome-mediated delivery, topical, nasal, sublingual, uretheral, intrathecal, ocular or otic delivery, implant, rectal, or intranasal.

While the components may be delivered via the same route, a product or pack described herein may contain a vinorelbine compound for delivery by a different route than that of an HKI-272 compound, e.g., one or more of the components may be delivered orally, while one or more of the others are administered intravenously. In one embodiment, the HKI-272 compound is prepared for oral delivery and the vinorelbine compound is prepared for intravenous delivery. In another embodiment, both the HKI-272 and vinorelbine compounds are prepared for intravenous delivery. In still another embodiment, both the HKI-272 and vinorelbine compounds are prepared for oral delivery. Optionally, other active components may be delivered by the same or different routes as the HKI-272 and/or vinorelbine compounds. Other variations would be apparent to one skilled in the art.

In still another embodiment, the compounds or components of the therapeutic regimen are administered once a week. In certain situations, dosing with the HKI-272 compound may be delayed or discontinued for a brief period (e.g., 1, 2 or three weeks) during the course of treatment. Such a delay or discontinuation may occur once, or more, during the course of treatment. The effective amount is known to one of skill in the art; it will also be dependent upon the form of the HKI-272 compound. One of skill in the art could routinely perform empirical activity tests to determine the bioactivity of the HKI-272 compound in bioassays and thus determine a suitable dosage to administer.

The HKI-272 and vinorelbine compounds or other optional compounds used in the combination and products described herein may be formulated in any suitable manner. However, the amounts of each compound in the unit dose can vary widely depending on the type of composition, regimen, size of a unit dosage, kind of excipients, and other factors well known to those of ordinary skill in the art. In one embodiment, the unit dose can contain, e.g., 0.000001 percent by weight (% w) to 10% w of either compound. In another embodiment the unit dose can contain about 0.00001% w to 1% w, with the remainder being the excipient or excipients.

The compositions described herein may be in a form suitable for oral administration, e.g., tablet, caplet, capsule, buccal forms, troches, lozenges and oral liquids, suspensions or solutions; parenteral injection (including intravenous, subcutaneous, intramuscular, intravascular or infusion), e.g., as a sterile solution, suspension or emulsion; topical administration, e.g., an ointment or cream; rectal administration, e.g., a suppository; or the route of administration may be by direct injection into the tumor or by regional delivery or by local delivery. In other embodiments, one or both components of the combination treatment may be delivered endoscopically, intratracheally, intralesionally, percutaneously, intravenously, subcutaneously, intraperitoneally or intratumorally. In general the compositions described herein may be prepared in a conventional manner using conventional excipients or carriers that are well known in the art. Pharmaceutical compositions for oral use may also be in the form of hard gelatin capsules in which the active ingredient is mixed with an inert solid excipient, e.g., calcium carbonate, calcium phosphate or kaolin, or as soft gelatin capsules in which the active ingredient is mixed with water or an oil, such as peanut oil, liquid paraffin or olive oil. In one embodiment, one or both of said vinorelbine compound and said HKI-272 compound are delivered orally to said subject.

Capsules may contain mixtures of the active compounds) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Useful tablet or caplet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine.

Oral formulations herein, e.g., tablets, caplets, or capsules described above, may utilize standard delay or time release formulations to alter the absorption of the active compound (s). The oral formulation may also consist of administering the active ingredient in water or a fruit juice, containing appropriate solubilizers or emulsifiers as needed.

In some cases it may be desirable to administer the compounds directly to the airways in the form of an aerosol.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol and liquid polyethylene glycol), suitable mixtures thereof, and vegetable oils. Preferred injectable formulations containing vinorelbine are described in the art. In one embodiment, the compounds may be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations may contain a preservative to prevent the growth of microorganisms. In one embodiment, one or both of the vinorelbine and HKI-272 compounds are delivered intravenously.

For use herein, transdermal administrations include all administrations across the surface of the body and the inner linings of bodily passages including epithelial and mucosal tissues. Such administrations may be performed using the present compounds, or pharmaceutically acceptable salts thereof, in lotions, creams, foams, patches, suspensions, solutions, and suppositories (rectal and vaginal). Transdermal administration may be accomplished through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

In another embodiment, one or both of the HKI-272 and vinorelbine compounds can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of one or more compound into the target cells in vivo. (See, e.g., Al-Muhammed, 3. Microencapsul. 13:293-306, 1996; Chonn, Curr. Opin. Biotechnol. 6:698-708, 1995; Ostro, Am. J. Hosp. Pharm. 46:1576-1587, 1989). In other cases, the preferred preparation of one or more of the components can be a lyophilized powder.

Encapsulating materials can also be employed with one or more of the compounds and the term "composition" can include the active ingredient in combination with an encapsulating material as a formulation, with or without other carriers. For example, the compounds can also be delivered as microspheres for slow release in the body. In one embodiment, microspheres can be administered via intradermal injection of drug-containing microspheres, which slowly release subcutaneously (see Rao, J. Biomater Sci. Polym. Ed. 7:623-645, 1995; as biodegradable and injectable gel formulations (see, e.g., Gao, Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months. Cachets can also be used in the delivery of the compounds of the present invention, e.g., anti-atherosclerotic medicaments.

Dosages of the HKI-272 Compound and Vinorelbine Compound

As is typical with oncology treatments, dosage regimens are closely monitored by the treating physician, based on numerous factors including the severity of the disease, response to the disease, any treatment related toxicities, age, and health of the patient. Dosage regimens are expected to vary according to the route of administration.

The dosages and schedules described hereinbefore may be varied according to the particular disease state and the overall condition of the patient. For example, it may be necessary or desirable to reduce the above-mentioned doses of the components of the combination treatment in order to reduce toxicity. Dosages and schedules may also vary if, in addition to a combination of an HKI-272 compound and a vinorelbine, one or more additional chemotherapeutic agents are used. Scheduling can be determined by the practitioner who is treating any particular patient using his professional skill and knowledge.

For the HKI-272 compound and/or vinorelbine compound, it is desired each compound of the combination of compounds is in the form of a unit dose. The term "unit dose" or "unit dose form" as used herein describes a single dose form including, without limitation, tablets, caplets, capsules, powders in sachets or vials, saline infusion bags, as described above.

Unit dose forms contain from about 0.1 to about 300 mg of a HKI-272 compound. In another embodiment, the unit dose form contains about 5 to about 300 mg of the HKI-272 compound. In another embodiment, the unit dose form contains about 50 to about 300 mg of the HKI-272 compound. In a further embodiment, the unit dose form contains about 75 to about 300 mg of the HKI-272 compound. In still a further embodiment, the unit dose form contains about 100 to about 300 mg of the HKI-272 compound. In yet another embodiment, the unit dose form contains about 120 to about 300 mg of the HKI-272 compound. In yet a further embodiment, the unit dose form contains about 160 to about 300 mg of the HKI-272 compound. In another embodiment, the unit dose form contains about 200 to about 300 mg of the HKI-272 compound. In yet another embodiment, the unit dose form contains about 240 to about 300 mg of the HKI-272 compound. In a further embodiment, the unit dose form contains about at least about 120 mg. In still a further embodiment, the unit dose form contains at least about 160 mg. In another embodiment, the unit dose form contains at least about 240 mg.

The HKI-272 compound can be administered, e.g., orally, at a dose range of about 0.01 to 100 mg/kg. In one embodiment, the HKI-272 compound is administered at a dose range of about 0.1 to about 90 mg/kg. In another embodiment, the HKI-272 compound is administered at a dose range of about 1 to about 80 mg/kg. In a further embodiment, the HKI-272 compound is administered at a dose range of about 10 to about 70 mg/kg. In yet another embodiment, the HKI-272 compound is administered at a dose range of about 15 to about 60 mg/kg. In still a further embodiment, the HKI-272 compound is administered at a dose range of about 20 to about 50 mg/kg. In another embodiment, the HKI-272 compound is administered at a dose range of about 30 to about 50 mg/kg. One of skill in the art could routinely perform empirical activity tests to determine the bioactivity of the compound in bioassays and thus determine what dosage to administer.

In one embodiment, the oral dosage of the HKI-272 compound is at least about 700 mg/week. In another embodiment, the oral dosage of the HKI-272 compound is about 800 mg/week to at least to about 1700 mg/week. In another embodiment, the oral dosage of the HKI-272 compound is about 840 mg/week to about 1680 mg/week. In another embodiment, the oral dosage of the HKI-272 compound is about 900 mg/week to about 1600 mg/week. In a further embodiment, the oral dosage of the HKI-272 compound is about 1000 mg/week to about 1500 mg/week. In yet another embodiment, the oral dosage of the HKI-272 compound is about 1100 mg/week to about 1400 mg/week. In still a further embodiment, the oral dosage of the HKI-272 compound is about 1200 mg/week to about 1300 mg/week. Precise dosages are determined by the administering physician based on experience with the individual subject to be treated. Other dosage regimens and variations are foreseeable, and are determined through physician guidance.

Desirably, the patient is administered about 0.1 to about 50 mg/kg of the vinorelbine compound. In one embodiment, the patient is administered about 1 to about 30 mg/kg of the vinorelbine compound. In another embodiment, the patient is administered about 5 to about 25 mg/kg of the vinorelbine compound. In a further embodiment, the patient is administered about 10 to about 20 mg/kg of the vinorelbine compound. In still a further embodiment, the patient is administered about 20 mg/kg of the vinorelbine compound.

Unit dose forms contain about 0.1 to about 100 mg of a vinorelbine compound. In another embodiment, the unit dose form contains about 1 to about 70 mg of the vinorelbine compound. In another embodiment, the unit dose form contains about 5 to about 500 mg of the vinorelbine compound. In a further embodiment, the unit dose form contains about 10 to about 250 mg of the vinorelbine compound. In still a further embodiment, the unit dose form contains about 15 to about 100 mg of the vinorelbine compound. In yet another embodiment, the unit dose form contains about 20 to about 75 mg of the vinorelbine compound. In yet a further embodiment, the unit dose form contains about 25 to about 50 mg of the vinorelbine compound. In another embodiment, the unit dose form contains about 30 to about 40 mg of the vinorelbine compound. In yet another embodiment, the unit dose form contains about 240 to about 300 mg of the vinorelbine compound. In a further embodiment, the unit dose form contains about at least about 120 mg. In still a further embodiment, the unit dose form contains at least about 160 mg. In another embodiment, the unit dose form contains at least about 240 mg.

In one embodiment, i.v. infusion dosages of the vinorelbine compound are from about 5 to about 25 mg/L. The initial infusion dosage of the vinorelbine compound may be more or less, as determined by the treating physician. In one embodiment, the i.v. infusion dosage of the vinorelbine compound is about 10 to about 20 mg/L. In a further embodiment, the i.v. infusion dosage of the vinorelbine compound is about 20 to about 25 mg/L. In yet another embodiment, the i.v. infusion dosage of the vinorelbine compound is at least about 10 mg/L. In another embodiment, the i.v. infusion dosage of the vinorelbine compound is at least about 15 mg/L. In yet another embodiment, the i.v. infusion dosage of the vinorelbine compound is at least about 20 mg/L. In yet another embodiment, the i.v. infusion dosage of the vinorelbine compound is at least about 25 mg/L. Precise dosages are determined by the administering physician based on experience with the individual subject to be treated. Other dosage regimens and variations are foreseeable, and are determined through physician guidance. In one embodiment, the vinorelbine compound is administered by i.v. infusion or orally, preferably in the form of tablets or capsules.

As described herein, subtherapeutically effective amounts of the HKI-272 compound and vinorelbine compound may be used to achieve a therapeutic effect when administered in combination. In one embodiment, the HKI-272 compound is provided at dosages of 5 to 50% lower when provided along with the vinorelbine compound. In another embodiment, the HKI-272 compound is provided at dosages of 10 to 25% lower when provided along with the vinorelbine compound. In a further embodiment, the HKI-272 compound is provided at dosages of 15 to 20% lower when provided along with the vinorelbine compound. In one embodiment, a resulting HKI-272 compound dosage is about 8 to 40 mg. In another embodiment, a resulting HKI-272 compound dosage is about 8 to 30 mg. In a further embodiment, a resulting HKI-272 compound dosage is about 8 to 25 mg. Subtherapeutically effective amounts of the HKI-272 compound and vinorelbine compound are expected to reduce the side-effects of treatment.

Alternatively, one or more of the active agents in the combination described herein is to be used in a supratherapeutic amount, i.e., at a higher dosage in the combination than when used alone. In this embodiment, the other active agent(s) are used in a therapeutic or subtherapeutic amount.

Regimen Using the HKI-272 Compound and Vinorelbine Compound

As used herein, the components of the therapeutic "combined" regimen, i.e., the HKI-272 compound and the vinorelbine compound, can be administered simultaneously. Alternatively, the two components can be administered in a staggered regimen, i.e., with the HKI-272 compound being given at a different time during the course of chemotherapy than the vinorelbine compound. This time differential may range from several minutes, hours, days, weeks, or longer between administration of the at least two agents. Therefore, the term combination (or combined) does not necessarily mean administered at the same time or as a unitary dose or single composition, but that each of the components are administered during a desired treatment period. The agents may also be administered by different routes. As used herein in one embodiment, 1 "cycle" includes 3 weeks.

These regimens or cycles may be repeated, or alternated, as desired. Other dosage regimens and variations are foreseeable, and are determined through physician guidance. The regimen may include "non-treatment" steps/visits including screening periods and post-treatment periods. In one embodiment, the regimen continues at least about 2 weeks, at least about 6 weeks, at least about 12 weeks, at least about 24 weeks, at least about 33 weeks, at least about 40 weeks, and at least about 46 weeks. Additional screening weeks and final monitoring weeks may also be included. For example, the regimen may include 4 weeks of screening and 6 weeks for final visit.

Single doses and multiple doses are contemplated. In one embodiment, the vinorelbine and/or HKI-272 compound is administered only once in the treatment. In another embodiment, the vinorelbine and/or HKI-272 compound is administered at least once over a period of 21 days. In a further embodiment, the vinorelbine and/or HKI-272 compound is administered at least twice over a period of 21 days. In still another embodiment, the vinorelbine and/or HKI-272 compound is administered on days 1, 2, 3, 4, 5, 6, 7, 8, 9, 10, 11, 12, 13, 14, 15, 16, 17, 18, 19, 20, and/or 21 of the cycle. In a further embodiment, the vinorelbine and/or HKI-272 compound is administered on days 1 and 8 of the cycle. In still a further embodiment, the vinorelbine and/or HKI-272 compound is administered at least once daily. In yet another embodiment, the vinorelbine and/or HKI-272 compound HKI-272 compound is administered on day 1. Desirably, the HKI-272 compound is administered on day 1 if the neoplasm is non-metastatic. In a further embodiment, the vinorelbine and/or HKI-272 compound is administered on day 2 of said regimen. Desirably, the HKI-272 compound is administered on day 2 if the neoplasm is metastatic. In still a further embodiment, the HKI-272 compound is administered orally at least once a day. In another embodiment, the HKI-272 compound is administered at least 1, 2, 3, 4, 5, or 6 times a day. In a further embodiment the HKI-272 compound is administered 1 to 4 times a day.

In one embodiment, a single loading dose of the vinorelbine compound and/or HKI-272 compound is administered. The single loading dose of the vinorelbine compound and/or the HKI-272 compound may be the same dose as the subsequent doses or the single loading dose may be greater than the dose administered to the patient throughout the remaining treatment. In a further embodiment, the vinorelbine compound/or the HKI-272 compound may be administered at a larger dose only once per cycle, i.e., one day per cycle.

If certain subjects do not tolerate one or more of the components of the composition, i.e., the HKI-272 compound or vinorelbine compound, or if the subject does not recover from treatment-related toxicity after more than 3 consecutive weeks, or if any grade 4 nonhematologic toxicity occurs that is treatment related, a dose reduction may be performed. In one embodiment, administration of one or both of the HKI-272 compound and the vinorelbine compound is discontinued if patent acquires one or more of a symptom including, without limitation, selected from the group consisting of neuropathy, neutropenia, thrombocytopenia, nausea, vomiting, decreased platelet count, and increased bilirubin count. In another embodiment, administration of one or both of the HKI-272 compound and the vinorelbine compound is discontinued or interrupted if the patient's neutrophil count of is less than about 1000/L. In a further embodiment, administration of one or both of the HKI-272 compound and the vinorelbine compound is discontinued or interrupted if the patient's platelet count is less than 75,000/L.

Alternatively, for those subjects do not tolerate one or more of the components of the composition, i.e., the HKI-272 compound or vinorelbine compound, dose reductions may be performed. In one embodiment, 1 or 2 dose reductions are performed. More desirably, only 1 dose reduction is performed.

For subjects who not recover from vinorelbine or HKI-272-related toxicity after more than 3 consecutive weeks, treatment with vinorelbine or HKI-272, respectively, may be discontinued. However, administration of the other agent, i.e., HKI-272 or vinorelbine, respectively, may be continued.

The regimen is typically continued for at least about 2 weeks. In one embodiment, the regimen is continued for no more than 46 weeks. In another embodiment, the regiment is continued for about 6 weeks. The length of participation is dependent on a subject's tolerance of the treatment and status of his or her disease. However, the treating physician may determine that shorter or longer treatment can be pursued. For example, subjects may receive more than 12 cycles of treatment if it is well tolerated, if the neoplasm has not progressed, if the subject is clinically stable, and if the subject has received an overall benefit.

In addition, the vinorelbine compound/or the HKI-272 compound may also be administered after completion of chemotherapy as maintenance therapy.

Pharmaceutical Packs and Kits

Also included is a product or pharmaceutical pack containing a course of an anti-neoplastic treatment for one individual mammal comprising one or more container(s) having one, one to four, or more unit(s) of the HKI-272 compound in unit dosage form and, optionally, one, one to four, or more unit(s) of the HKI-272 and vinorelbine compounds, and optionally, another active agent. The combinations may be in the form of a kit of parts.

In one embodiment a kit includes a first container with a suitable composition containing a HKI-272 compound and a second container with a suitable composition containing a vinorelbine compound. Accordingly, there is provided a kit for use in the treatment or prophylaxis of cancer. This kit includes comprising: a) HKI-272 compound together with a pharmaceutically-acceptable excipient or carrier, in a first unit dosage form; b) a vinorelbine compound together with a pharmaceutically-acceptable excipient or carrier, in a second unit dosage form; and c) a container for containing said first and second dosage forms.

In another embodiment, pharmaceutical packs contain a course of anti-neoplastic treatment for one individual mammal comprising a container having a unit of a HKI-272 compound in unit dosage form, a containing having a unit of a vinorelbine compound, and optionally, a container with another active agent.

In some embodiments, the compositions are in packs in a form ready for administration. In other embodiments, the compositions are in concentrated form in packs, optionally with the diluent required to make a final solution for administration. In still other embodiments, the product contains a compound described herein in solid form and, optionally, a separate container with a suitable solvent or carrier.

In still other embodiments, the above packs/kits include other components, e.g., instructions for dilution, mixing and/or administration of the product, other containers, syringes, needles, etc. Other such pack/k it components are readily apparent to one of skill in the art.

Concurrent Treatments

In addition to the optional chemotherapeutic agents and optional compounds noted above, the regimens and methods described herein can be performed prior to, concurrently with, or subsequent to other non-medication procedures. In one embodiment, radiation may be performed prior to, concurrently with, or subsequent to treatment with the HKI-272 and vinorelbine compounds.

Preferred Embodiments

In one embodiment, a regimen for treating a solid tumor associated with overexpression or amplification of HER-2 in a subject is provided. One cycle of the regimen includes 21 days and the regimen includes orally administering at least one unit dose of HKI-272 starting on day 1 of the cycle and intravenously administering at least one a unit dose of vinorelbine on days 1 and 8 of the cycle.

In another embodiment, a regimen for treating a metastatic cancer associated with overexpression or amplification of HER-2 in a subject is provided. One cycle of the regimen includes 21 days and the regimen includes orally administering at least one unit dose of HKI-272 starting on day 2 of the cycle and intravenously administering at least one unit dose of vinorelbine on days 1 and 8 of the cycle.

In a further embodiment, a product containing vinorelbine and HKI-272 is provided. The product is useful as a combined preparation for simultaneous, separate or sequential use in treating a neoplasm in a mammal.

In still a further embodiment, a pharmaceutical pack for treating a neoplasm in one individual mammal is provided. The pharmaceutical pack contains at least one unit of vinorelbine and at least one unit of HKI-272.

In another embodiment, a pharmaceutical composition is provided and contains vinorelbine, HKI-272, and at least one pharmaceutically acceptable carrier. Desirably, the pharmaceutical composition is useful for treating a neoplasm in a mammal.

In still another embodiment, a method of treating a neoplasm associated with overexpression or amplification of HER-2 in a mammal in need thereof is provided. The method includes administering a unit dose of a vinorelbine compound and administering a unit dose of a HKI-272 compound.

The following examples illustrate of the uses of the combinations of the invention. It will be readily understood that alterations or modifications, e.g., in the formulation of the components, the routes of delivery, and the dosing, can be made for reasons known to those of skill in the art.

Example 1

Combination Regimen of HKI-272 and Vinorelbine in Lung Cancer Cell Proliferation Assays A standard cell proliferation assay was utilized to independently analyze the response of lung cell lines NCI-H1666, NCI-H1650, and NCI-H1975 to various dilutions of HKI-272 and vinorelbine in combination. Briefly, fetal bovine serum (FBS) RPM1-1640 (Media) was added to each well of 96 well plates containing one of the cell lines. Each column of wells contained a different dilution of HKI-272 and solutions of vinorelbine were added to each well at a variety of dilutions with respect to the HKI-272 dilutions (the highest final concentration of HKI-272 was 1 μM for the H1650 and H1666 cell lines; the highest final concentration of HKI-272 was 9 μM for the H1975 cell line; and the highest final concentration of vinorelbine was 0.1 μM for all of the cell lines). Following incubation of the cell plates at 37° C., 5% $CO_2$ for 72 hours, cell proliferation was assessed.

Cell proliferation was reduced after incubation with HKI-272 and vinorelbine.

Example 2

Combination Regimen of HKI-272 and Vinorelbine in Treatment of Non-Metastatic Breast Cancers Patients having diagnosed non-metastatic breast cancers are treated using a regimen of HKI-272 and vinorelbine. Patients are administered HKI-272 at either dose level 1 or 2. Dosing of HKI-272 begins at cycle 1, day 1 with daily oral administration of HKI-272 at the dosages in Table 3. HKI-272 is taken orally on the remaining days of the each cycle. On those days that HKI-272 and vinorelbine are administered on the same day, i.e., days 1 and 8 of the cycle, HKI-272 is administered prior to the vinorelbine infusion.

TABLE 3

| Dose Level | HKI-272 Dose (mg) | Vinorelbine Dose $(mg/m^2)$ |
| --- | --- | --- |
| 1 | 160 | 25 |
| 2 | 240 | |

Vinorelbine is administered on days 1 and 8 of each 21-day cycle, provided that the combination of HKI-272 and vinorelbine is well tolerated and there is no evidence of disease progression. Vinorelbine is administered intravenously using preferentially a central venous route, through a free-flowing IV line over approximately 10 minutes, followed by 125 mL of saline solution infused over approximately 30 minutes.

If the patient has any serious side-effects during the treatment, dose adjustments of HKI-272 and/or vinorelbine are permitted. See, Tables 4 and 5.

TABLE 4

| Dose Adjustment | HKI-272 (mg) |
| --- | --- |
| $-1^a$ | 120 |
| $1^b$ | 160 |
| 2 | 240 |

$^a$The −1 dose level is used only if dose reduction is required.
$^b$The dose 1 level is to be used as first level of dose reduction in case the defined maximum tolerated dose is 240 mg.

TABLE 5

| Dose Adjustment | Vinorelbine $(mg/m^2)$ |
| --- | --- |
| $-1^a$ | 20 |
| 1 | 25 |

$^a$The −1 dose level is to be used only if dose reduction is needed.

It is predicted that a decrease in tumor growth will be observed.

Example 3

Combination Regimen of HKI-272 and Vonorelbine in Treatment of Metastatic Breast Cancers Patients having diagnosed metastatic breast cancers are treated using a regimen of HKI-272 and vinorelbine.

Vinorelbine is administered on day 1 and day 8 of the cycle using the dosages described in Example 2, Table 3 or 5. The vinorelbine is administered over a 30-minute period using an in-line filter and an automatic dispensing pump. Optionally, antihistamine (diphenhydramine, 25 to 50 mg IV or the equivalent) is administered about 30 minutes prior to vinorelbine infusion.

Dosing of HKI-272 begins at cycle 1, day 2 with daily oral administration of HKI-272 at the dosages provided in Example 2, Table 3 or 4. HKI-272 is taken orally on the remaining days of the each cycle. On those days that HKI-272 and vinorelbine are administered on the same day, i.e., day 8 of the cycle, HKI-272 is administered prior to the vinorelbine infusion. If the patient has any serious side-effects during the treatment, the dose adjustments of HKI-272 and/or vinorelbine are permitted.

It is predicted that a decrease in tumor growth will be observed.

All patents, patent publications, articles, and other documents referenced herein are incorporated by reference. It will be clear to one of skill in the art that modifications can be made to the specific embodiments described herein without departing from the scope of the invention.

What is claimed is:

1. A method for treating a neoplasm in a patient in need thereof, consisting of administering to the patient:
    i) an effective amount of (E)-N-{4-[3-chloro-4-(2-pyridinylmethoxy)anilino]-3-cyano-7-ethoxy-6-quinolinyl}-4-(dimethylamino)-2-butenamide, or an ester, ether, carbamate, or a pharmaceutically acceptable salt thereof; and
    ii) vinorelbine, or a pharmaceutically acceptable salt thereof;
wherein the neoplasm is selected from the group consisting of a lung cancer and breast cancer.

2. The method of claim 1, wherein the method administers an effective amount of (E)-N-{4-[3-chloro-4-(2-pyridinylmethoxy)anilino]-3-cyano-7-ethoxy-6-quinolinyl}-4-(dimethylamino)-2-butenamide, or a pharmaceutically acceptable salt thereof.

3. The method of claim 2, wherein the (E)-N-{4-[3-chloro-4-(2-pyridinylmethoxy) anilino]-3-cyano-7-ethoxy-6-quinolinyl}-4-(dimethylamino)-2-butenamide, or pharmaceutically acceptable salt thereof, is administered in a unit dose.

4. The method of claim 3, wherein said unit dose is a tablet.

5. The method of claim 2, wherein one or both of the (E)-N-{4-[3-chloro-4-(2-pyridinylmethoxy)anilino]-3-cyano-7-ethoxy-6-quinolinyl}-4-(dimethylamino)-2-butenamide, or pharmaceutically acceptable salt thereof, and the vinorelbine are delivered intravenously or orally to said patient.

6. The method of claim 2, wherein the (E)-N-{4-[3-chloro-4-(2-pyridinylmethoxy) anilino]-3-cyano-7-ethoxy-6-quinolinyl}-4-(dimethylamino)-2-butenamide, or pharmaceutically acceptable salt thereof, is administered in an amount of at least about 120 mg.

7. The method of claim 6, wherein the (E)-N-{4-[3-chloro-4-(2-pyridinylmethoxy) anilino]-3-cyano-7-ethoxy-6-quinolinyl}-4-(dimethylamino)-2-butenamide, or pharmaceutically acceptable salt thereof, is administered in an amount of at least about 160 mg.

8. The method of claim 7, wherein the (E)-N-{4-[3-chloro-4-(2-pyridinylmethoxy) anilino]-3-cyano-7-ethoxy-6-quinolinyl}-4-(dimethylamino)-2-butenamide, or pharmaceutically acceptable salt thereof, is administered in an amount of at least about 240 mg.

9. The method of claim 2, wherein the (E)-N-{4-[3-chloro-4-(2-pyridinylmethoxy) anilino]-3-cyano-7-ethoxy-6-quinolinyl}-4-(dimethylamino)-2-butenamide, or pharmaceutically acceptable salt thereof, is administered daily.

10. The method of claim 2, wherein the (E)-N-{4-[3-chloro-4-(2-pyridinylmethoxy) anilino]-3-cyano-7-ethoxy-6-quinolinyl}-4-(dimethylamino)-2-butenamide, or pharmaceutically acceptable salt thereof, is administered at least once daily.

11. The method of claim 2, wherein the (E)-N-{4-[3-chloro-4-(2-pyridinylmethoxy) anilino]-3-cyano-7-ethoxy-6-quinolinyl}-4-(dimethylamino)-2-butenamide, or pharmaceutically acceptable salt thereof, is administered on day 1 of said regimen.

12. The method of claim 2, wherein the (E)-N-{4-[3-chloro-4-(2-pyridinylmethoxy) anilino]-3-cyano-7-ethoxy-6-quinolinyl}-4-(dimethylamino)-2-butenamide, or pharmaceutically acceptable salt thereof, is administered for at least 2 continuous weeks.

13. The method of claim 2, wherein the method administers vinorelbine.

14. The method of claim 13, wherein the vinorelbine is administered in a unit dose.

15. The method of claim 13, wherein the vinorelbine is administered in an amount of at least about 20 mg/L.

16. The method of claim 13, wherein the vinorelbine is administered in an amount of about 20 to about 25 mg/L.

17. The method of claim 2, wherein the administering steps occur concurrently, sequentially, simultaneously, in a specified order, or according to a specific temporal relationship.

18. The method of claim 2, wherein the neoplasm is metastatic.

19. The method of claim 2, wherein the neoplasm is an advanced solid tumor.

20. The method of claim 2, wherein the patient has a neutrophil count of at least 1500, a platelet count of at least 100,000/L, or both.

21. The method of claim 13, wherein the vinorelbine is administered in an amount of between 5-500 mg.

22. The method of claim 2, wherein the neoplasm overexpresses or amplifies HER-2.

23. The method of claim 2, wherein the neoplasm is lung cancer.

24. The method of claim 2, wherein the neoplasm is breast cancer.

25. The method of claim 2, wherein the neoplasm is metastatic breast cancer.

26. A method for treating a HER-2 positive breast cancer in a patient in need thereof, consisting of administering to the patient:
    i) an effective amount of (E)-N-{4-[3-chloro-4-(2-pyridinylmethoxy)anilino]-3-cyano-7-ethoxy-6-quinolinyl}-4-(dimethylamino)-2-butenamide, or an ester, ether, carbamate, or a pharmaceutically acceptable salt thereof; and
    ii) vinorelbine, or a pharmaceutically acceptable salt thereof.

27. The method of claim 26, wherein the method administers an effective amount of (E)-N-{4-[3-chloro-4-(2-pyridinylmethoxy)anilino]-3-cyano-7-ethoxy-6-quinolinyl}-4-(dimethylamino)-2-butenamide, or a pharmaceutically acceptable salt thereof.

28. The method of claim 27, wherein the (E)-N-{4-[3-chloro-4-(2-pyridinylmethoxy) anilino]-3-cyano-7-ethoxy-6-quinolinyl}-4-(dimethylamino)-2-butenamide, or pharmaceutically acceptable salt thereof, is administered in a unit dose.

29. The method of claim 28, wherein said unit dose is a tablet.

30. The method of claim 27, wherein one or both of the (E)-N-{4-[3-chloro-4-(2-pyridinylmethoxy)anilino]-3-cyano-7-ethoxy-6-quinolinyl}-4-(dimethylamino)-2-butenamide, or pharmaceutically acceptable salt thereof, and the vinorelbine are delivered intravenously or orally to said patient.

31. The method of claim 27, wherein the (E)-N-{4-[3-chloro-4-(2-pyridinylmethoxy) anilino]-3-cyano-7-ethoxy-6-quinolinyl}-4-(dimethylamino)-2-butenamide, or pharmaceutically acceptable salt thereof, is administered in an amount of at least about 120 mg.

32. The method of claim 31, wherein the (E)-N-{4-[3-chloro-4-(2-pyridinylmethoxy) anilino]-3-cyano-7-ethoxy-6-quinolinyl}-4-(dimethylamino)-2-butenamide, or pharmaceutically acceptable salt thereof, is administered in an amount of at least about 160 mg.

33. The method of claim 32, wherein the (E)-N-{4-[3-chloro-4-(2-pyridinylmethoxy) anilino]-3-cyano-7-ethoxy-6-quinolinyl}-4-(dimethylamino)-2-butenamide, or pharmaceutically acceptable salt thereof, is administered in an amount of at least about 240 mg.

34. The method of claim 27, wherein the (E)-N-{4-[3-chloro-4-(2-pyridinylmethoxy) anilino]-3-cyano-7-ethoxy-6-quinolinyl}-4-(dimethylamino)-2-butenamide, or pharmaceutically acceptable salt thereof, is administered daily.

35. The method of claim 27, wherein the (E)-N-{4-[3-chloro-4-(2-pyridinylmethoxy) anilino]-3-cyano-7-ethoxy-6-quinolinyl}-4-(dimethylamino)-2-butenamide, or pharmaceutically acceptable salt thereof, is administered at least once daily.

36. The method of claim 27, wherein the (E)-N-{4-[3-chloro-4-(2-pyridinylmethoxy) anilino]-3-cyano-7-ethoxy-6-quinolinyl}-4-(dimethylamino)-2-butenamide, or pharmaceutically acceptable salt thereof, is administered on day 1 of said regimen.

37. The method of claim 27, wherein the (E)-N-{4-[3-chloro-4-(2-pyridinylmethoxy) anilino]-3-cyano-7-ethoxy-6-quinolinyl}-4-(dimethylamino)-2-butenamide, or pharmaceutically acceptable salt thereof, is administered for at least 2 continuous weeks.

38. The method of claim 27, wherein the method administers vinorelbine.

39. The method of claim 38, wherein the vinorelbine is administered in a unit dose.

40. The method of claim 38, wherein the vinorelbine is administered in an amount of at least about 20 mg/L.

41. The method of claim 38, wherein the vinorelbine is administered in an amount of about 20 to about 25 mg/L.

42. The method of claim 38, wherein the vinorelbine is administered in an amount of between 5-500 mg.

43. The method of claim 27, wherein the administering steps occur concurrently, sequentially, simultaneously, in a specified order, or according to a specific temporal relationship.

44. The method of claim 27, wherein the HER-2 positive breast cancer is HER-2 positive metastatic breast cancer.

45. The method of claim 27, wherein the HER-2 positive breast cancer is an advanced solid tumor.

46. The method of claim 27, wherein the patient has a neutrophil count of at least 1500, a platelet count of at least 100,000/L, or both.

* * * * *